(12) United States Patent
Riess et al.

(10) Patent No.: US 10,408,810 B2
(45) Date of Patent: Sep. 10, 2019

(54) METHODS AND APPARATUS FOR DETERMINING FERTILIZER/TREATMENT REQUIREMENTS AND/OR PREDICTING PLANT GROWTH RESPONSE

(71) Applicant: UNIBEST INTERNATIONAL, LLC, Walla Walla, WA (US)

(72) Inventors: Mark James Riess, Walla Walla, WA (US); Brennan Allan Ingram, Walla Walla, WA (US); Kristopher James Borgman, Walla Walla, WA (US); Robert Gabriel Melanson, Juneau, AK (US); Jennifer Ann Chapman, Walla Walla, WA (US); Ivan Rozumny, Walla Walla, WA (US)

(73) Assignee: UNIBEST INTERNATIONAL, LLC, Kennewick, WA (US)

( * ) Notice: Subject to any disclaimer, the term of this patent is extended or adjusted under 35 U.S.C. 154(b) by 297 days.

(21) Appl. No.: 15/059,255

(22) Filed: Mar. 2, 2016

(65) Prior Publication Data
US 2017/0045488 A1 Feb. 16, 2017

Related U.S. Application Data

(60) Provisional application No. 62/127,115, filed on Mar. 2, 2015, provisional application No. 62/127,146, filed on Mar. 2, 2015, provisional application No. 62/127,181, filed on Mar. 2, 2015.

(51) Int. Cl.
*G01N 33/24* (2006.01)
*A01C 21/00* (2006.01)

(52) U.S. Cl.
CPC .......... *G01N 33/24* (2013.01); *A01C 21/007* (2013.01); *G01N 2033/245* (2013.01)

(58) Field of Classification Search
CPC .... A01C 21/007; G01N 33/24; G01N 33/246; G01N 2033/245
USPC ............................... 436/25, 28, 39; 800/295
See application file for complete search history.

(56) References Cited

U.S. PATENT DOCUMENTS

| 4,345,484 A | 8/1982 | Gould et al. |
| 4,438,654 A | 3/1984 | Torstensson |
| 4,827,776 A | 5/1989 | Gale et al. |
| 4,857,473 A | 8/1989 | Magaritz et al. |
| 4,976,866 A | 12/1990 | Grinstead et al. |

(Continued)

*Primary Examiner* — Maureen Wallenhorst
(74) *Attorney, Agent, or Firm* — Pedersen and Company, PLLC; Ken J. Pedersen; Barbara S. Pedersen

(57) ABSTRACT

A soil testing method determines available nutrient levels and effective and economical fertilizer/treatment, based on what nutrients in the soil will actually reach the root of a growing plant. A soil is tested to determine initial nutrient(s) available to a plant root if it were growing in that soil when no nutrients have been added, followed by comparing/correlating the initial available nutrient to nutrient requirements for desired plant growth during one or more periods of time and/or to a yield outcome desired. Various doses of fertilizer(s) or treatment(s) are then added to portions of the soil, and those dosed portions are then tested for available nutrient levels, to determine the effect of the fertilizer(s)/treatment(s) on the nutrients that would be available in that particular soil to a plant root if that soil were fertilized with the various doses.

8 Claims, 48 Drawing Sheets

(56) References Cited

U.S. PATENT DOCUMENTS

| | | |
|---|---|---|
| 5,149,436 A | 9/1992 | Taniguchi et al. |
| 5,322,388 A | 6/1994 | Wells |
| 5,355,736 A | 10/1994 | Skogley |
| 5,834,633 A | 11/1998 | Davison |
| 6,112,602 A | 9/2000 | Mitra |
| 6,242,261 B1 | 6/2001 | Schoenau et al. |
| 6,324,922 B1 * | 12/2001 | Hanks ................. G01N 1/34 422/68.1 |
| 6,401,547 B1 | 6/2002 | Hatfield et al. |
| 7,325,443 B2 | 2/2008 | De Jonge et al. |
| 7,399,447 B2 | 7/2008 | Bowers et al. |
| 7,992,430 B2 | 8/2011 | De Jonge |
| 8,763,478 B2 | 7/2014 | Riess et al. |
| 2008/0105064 A1 | 5/2008 | Halland |
| 2009/0007704 A1 | 1/2009 | Bowers et al. |
| 2009/0084976 A1 | 4/2009 | Camilli |
| 2010/0031759 A1 | 2/2010 | Tovena-Pecault |
| 2012/0222500 A1 | 9/2012 | Riess et al. |
| 2014/0069184 A1 | 3/2014 | McAlary et al. |
| 2014/0165713 A1 * | 6/2014 | Frey ................. A01B 79/005 73/64.56 |
| 2015/0075299 A1 | 3/2015 | Riess et al. |

* cited by examiner

After the UNIBEST Method, sample results are determined

Reported baseline nutrients and recommended fertilizer trials

| Grower: | | | Date of Sample: | | | | Yield Goal: | 200 |
|---|---|---|---|---|---|---|---|---|
| Effective Rooting Depth (in): | 24 | | 6/16/2014 | | | | Growth Stage at | |
| Target Range* | | Total N | B | Ca | Cu | Fe | K (K2O) | |
| Total Rooting Profile Requirements (lb/ac): | | 190-258 | 0.46-0.62 | 24-33 | 0.14-0.18 | 0.68-0.92 | 230-311 | |
| Total Sample Depth: 24" | Zone Low #1 | 142.66 | 1.78 | 1348.88 | 0.72 | 4.12 | 347.38 | |
| | Deficit (lb/ac): | 81.34 | -1.24 | -13.48 | -0.56 | -3.32 | -77.38 | |
| Total Sample Depth: 24" | Zone High #2 | 172.75 | 0.81 | 166.69 | 0.39 | 2.48 | 693.35 | |
| | Deficit (lb/ac): | 51.25 | -0.27 | -166.69 | -0.23 | -1.68 | -423.35 | |
| Total Sample Depth: 24" | Zone Med #3 | 196.93 | 1.30 | 377.54 | 0.22 | 1.33 | 456.03 | |
| | Deficit (lb/ac): | 27.07 | -0.76 | -377.54 | -0.07 | -0.53 | -186.03 | |
| TOTAL AVERAGE DEFICIT (LB/AC): | | 53.22 | (0.76) | (185.90) | (0.29) | (1.84) | (228.92) | |
| GREATEST DEFICIT (LB/AC): | | 81.34 | (0.27) | (13.48) | (0.07) | (0.53) | (77.38) | |

Fig. 8A

| bu/ac | | Farm Name: | | Crop: | |
|---|---|---|---|---|---|
| Sampling: | | V3 | | | CORN |
| Mg | Mn | P (P2O5) | S (SO4) | Zn | |
| 40-54 | 1.39-1.89 | 87-117 | 26-35 | 0.44-0.6 | |
| 606.68 | 2.21 | 144.07 | 29.76 | 0.51 | |
| -606.15 | -0.57 | -42.07 | 0.24 | 0.01 | |
| 203.98 | 1.43 | 92.84 | 26.37 | 0.76 | |
| -203.46 | 0.21 | 9.16 | 3.63 | -0.24 | |
| 262.01 | 1.66 | 56.86 | 25.82 | 0.25 | |
| -261.49 | -0.02 | 45.14 | 4.18 | 0.27 | |
| (357.03) | (0.13) | 4.08 | 2.68 | 0.01 | |
| (203.46) | 0.21 | 45.14 | 4.18 | 0.27 | |

Fig. 8B

"Try Before You Apply" Fertilizer Application Recommendation

Initial Nutrient Summary

| | Total N | B | Ca | Cu | Fe | K | Mg | Mn |
|---|---|---|---|---|---|---|---|---|
| Nutrient Requirements (lb/ac) | 190-258 | 0.46-0.62 | 24-33 | 0.14-0.18 | 0.68-0.92 | 230-311 | 40-54 | 1.39-1.89 |
| Initial Nutrient Deficits (lb/ac) | 49.53 | -0.12 | -403.34 | -0.36 | -2.88 | -245.62 | -198.53 | 0.31 |

Laboratory Trial Results

| | Post-Application Nutrient Deficit (lb/ac) | | | | | | | |
|---|---|---|---|---|---|---|---|---|
| | Total N | B | Ca | Cu | Fe | K | Mg | Mn |
| Nutrient Requirements (lb/ac) | 190-258 | 0.46-0.62 | 24-33 | 0.14-0.18 | 0.68-0.92 | 230-311 | 40-54 | 1.39-1.89 |
| Fertilizer Application Rate A | 39.234 | -0.16 | -452.56 | -0.41 | -3.02 | -260.32 | -203.32 | 0.22 |
| Fertilizer Application Rate B | 27.09 | -0.18 | -530.93 | -0.45 | -3.45 | -274.89 | -210.45 | 0.09 |
| Fertilizer Application Rate C | 5.82 | -0.23 | -580.03 | -0.49 | -3.78 | -289.24 | -223.9 | -0.01 |
| *Fertilizer Application Rate D* | *-10.58* | *-0.26* | *-603.29* | *-0.51* | *-3.98* | *-301.23* | *-230.43* | *-0.12* |
| Fertilizer Application Rate E | -20.53 | -0.31 | -693.02 | -0.55 | -4.21 | -345.32 | -249.49 | -0.19 |

Recommendation

| Optimal Fertilizer Application | Fertilizer Application Rate D: 325 (lb/ac) |
|---|---|

*Fig. 10A*

| P | S | Zn |
|---|---|---|
| 87-117 | 26-35 | 0.44-0.6 |
| 23.52 | 2.49 | 0.12 |

| P | S | Zn |
|---|---|---|
| 87-117 | 26-35 | 0.44-0.6 |
| 8.43 | 1.94 | 0.04 |
| -1.36 | 1.23 | 0 |
| -8.38 | 0.3 | -0.02 |
| -15.54 | -1.34 | -0.16 |
| -24.32 | -1.78 | -0.17 |

Fig. 10B

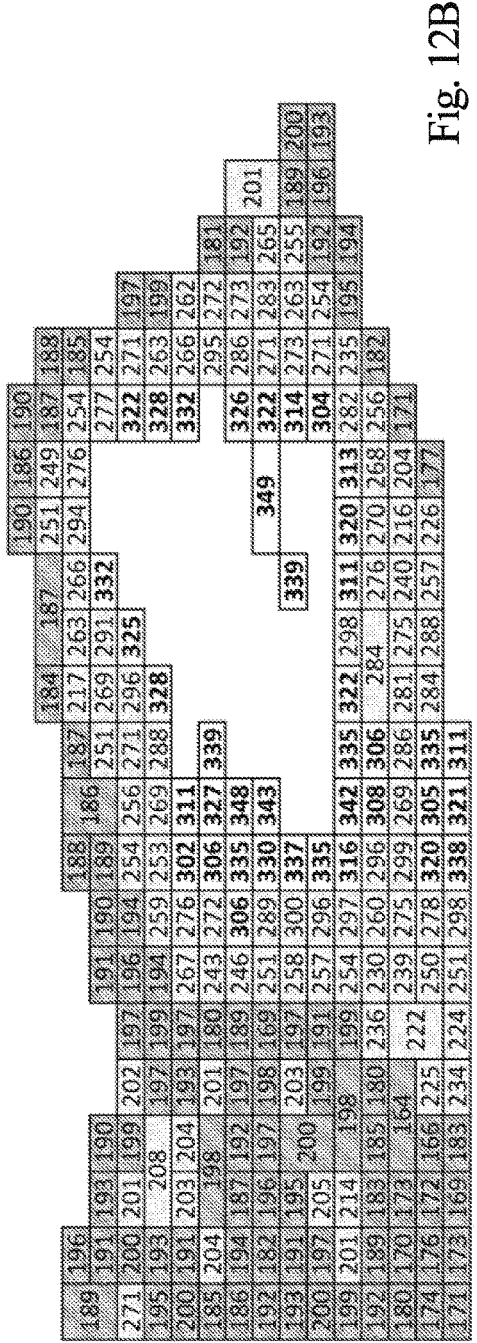
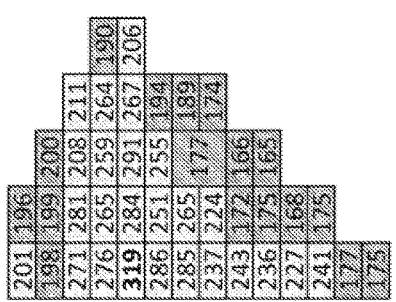
Fig. 12B

Example Nutrient Deficit Algorithm $$\text{Nitrogen Deficit(lb/ac)} = \underbrace{[(\text{Yield Goal}) * (\text{Crop-Specific Multiplier})]}_{\text{Required Nitrogen (lb/ac)}} - \underbrace{[(\text{Resin ppm}) * (\text{Depth Multiplier}) * (\text{Soil Type Multiplier})]}_{\text{Available Nitrogen (lb/ac)}}$$

General Formula:

$$\text{Concentration Deviation} = (\text{Optimal Concentration}) - \underbrace{f(\text{Resin ppm, Parameter(s)})}_{\text{Available Concentration}}$$

Fig. 16

Example Algorithm for Fertilizer Application Rate:

$$\text{Fertilizer Application Rate (lb/ac)} = \begin{pmatrix} \text{Nutrient} \\ \text{Deficit} \end{pmatrix} * \begin{pmatrix} \text{Bulk Density} \\ \text{Multiplier} \end{pmatrix} * \begin{pmatrix} \text{Fertilizer Type} \\ \text{Multiplier} \end{pmatrix}$$

General Formula:

$$\text{Predicted Amendment} = f(\text{Concentration Deviation. Parameter(s)})$$

Fig. 17

Example Algorithm for Soil Response to Fertilizer Application:

$$\text{Projected Soil Nutrient Level (lb/ac)} = \begin{pmatrix} \text{Available} \\ \text{Nutrients} \end{pmatrix} + \underbrace{\begin{pmatrix} \text{Fertilizer} \\ \text{Application Rate} \end{pmatrix} + \begin{pmatrix} \text{"Try Before You Apply"} \\ \text{Soil Response Multiplier} \end{pmatrix}}_{\text{Nutrients Available to Plant from Fertilizer Application}}$$

General Formula:

$$\text{Predicted Outcome} = f(\text{Procedural Ammendment(s), Parameter(s)})$$

Fig. 18 ppm values received from UNIBEST analysis:
ppm→lb/ac: ppm * depth of sample * soil classification nutrient multiplier

| Zone 1: | | Total N | NO3-N | NH4-N | Al | B | Ca | Cu | Fe | K (K2O) |
|---|---|---|---|---|---|---|---|---|---|---|
| 0-12" | ppm: | 25.66 | 21.07 | 4.59 | 4.02 | 0.11 | 98.96 | 0.05 | 0.93 | 10.98 |
| | lb/ac: | 101.61 | 0.00 | 0.00 | 0.00 | 1.25 | 142.51 | 0.26 | 1.90 | 85.62 |
| 12-24" | ppm: | 8.08 | 3.41 | 4.67 | 2.35 | 0.09 | 81.39 | 0.03 | 0.81 | 4.66 |
| | lb/ac: | 31.99 | 0.00 | 0.00 | 0.00 | 1.08 | 117.20 | 0.15 | 1.66 | 36.38 |
| | Total lb/ac | 133.60 | * | * | * | 2.33 | 259.71 | 0.42 | 3.56 | 122.01 |
| Zone 2: | | Total N | NO3-N | NH4-N | Al | B | Ca | Cu | Fe | K (K2O) |
| 0-12" | ppm: | 18.75 | 13.87 | 4.88 | 3.42 | 0.05 | 110.56 | 0.02 | 0.62 | 17.88 |
| | lb/ac: | 74.26 | 0.00 | 0.00 | 0.00 | 0.56 | 159.21 | 0.14 | 1.26 | 139.45 |
| 12-24" | ppm: | 8.01 | 4.68 | 3.33 | 1.06 | 0.06 | 135.57 | 0.01 | 0.36 | 6.04 |
| | lb/ac: | 31.71 | 0.00 | 0.00 | 0.00 | 0.68 | 195.22 | 0.08 | 0.73 | 47.11 |
| | Total lb/ac | 105.97 | * | * | * | 1.24 | 354.43 | 0.22 | 1.99 | 186.56 |

Soil Classification Nutrient Multipliers:

| Soil Type: | | Total N | | | | B | Ca | Cu | Fe | K |
|---|---|---|---|---|---|---|---|---|---|---|
| Heavy Soil | per 1" | 0.29 | | | | 0.83 | 0.1 | 0.42 | 0.14 | 0.57 |
| Light Soil | per 1" | 0.33 | | | | 0.95 | 0.12 | 0.48 | 0.17 | 0.65 |

Total N for Zone 1: 25.66(ppm) * 0.29 (soil nutrient multiplier) * 12 (depth of sample) = 89.29

Fig. 21A

|       | Mg     | Mn   | Na   | P (P2O5) | S (SO4) | Zn   |
|-------|--------|------|------|----------|---------|------|
|       | 20.71  | 2.04 | 2.60 | 2.91     | 2.77    | 0.05 |
|       | 131.70 | 4.16 | 0.00 | 37.69    | 8.31    | 0.62 |
|       | 14.52  | 1.14 | 2.04 | 2.50     | 2.91    | 0.03 |
|       | 92.34  | 2.32 | 0.00 | 32.39    | 8.74    | 0.35 |
|       | 224.04 | 6.47 | *    | 70.08    | 17.05   | 0.97 |
|       | Mg     | Mn   | Na   | P (P2O5) | S (SO4) | Zn   |
|       | 10.05  | 2.41 | 0.70 | 3.28     | 2.00    | 0.05 |
|       | 63.94  | 4.92 | 0.00 | 42.54    | 6.01    | 0.61 |
|       | 14.45  | 0.43 | 1.39 | 1.73     | 2.70    | 0.02 |
|       | 91.88  | 0.87 | 0.00 | 22.46    | 8.09    | 0.23 |
|       | 155.82 | 5.79 | *    | 65.00    | 14.10   | 0.84 |

| Mg   | Mn   | P    | S    | Zn   |
|------|------|------|------|------|
| 0.46 | 0.14 | 0.94 | 0.22 | 0.83 |
| 0.53 | 0.17 | 1.08 | 0.25 | 0.95 |

*Fig. 21B*

Sample Report of Available Nutrients

| Test | Target Range* | | Total N | NO3-N | NH4-N | Al | B | Ca |
|---|---|---|---|---|---|---|---|---|
| Total Rooting Profile Requirements (lb/ac): | 190-258 | | | * | * | * | 0.46-0.62 | 24-33 |
| Barcode | Sample ID: | Depth (in): | | | | | | |
| | | | | | | | | Zone 1 |
| #2106785 | #1 | 0-12 | 25.66 | 21.07 | 4.59 | 4.02 | 0.11 | 98.96 |
| #2106786 | #2 | 12-24 | 8.08 | 3.41 | 4.67 | 2.35 | 0.09 | 81.39 |
| | | Total Profile (ppm): | 33.74 | 24.48 | 9.26 | 6.37 | 0.20 | 180.36 |
| | **Total Available Nutrients (lb/ac): | | 117.40 | * | * | * | 2.03 | 216.43 |
| | | | | | | | | Zone 2 |
| #2106784 | #3 | 0-12 | 18.75 | 13.87 | 4.88 | 3.42 | 0.05 | 110.56 |
| #2106783 | #4 | 12-24 | 8.01 | 4.68 | 3.33 | 1.06 | 0.06 | 135.57 |
| | | Total Profile (ppm): | 26.76 | 18.55 | 8.21 | 4.48 | 0.11 | 246.13 |
| | **Total Available Nutrients (lb/ac): | | 93.12 | * | * | * | 1.08 | 295.36 |

Fig. 22A

| Cu 0.14-0.18 | Fe 0.68-0.92 | K (K2O) 230-311 | Mg 40-54 | Mn 1.39-1.89 | Na * | P (P2O5) 87-117 | S (SO4) 26-35 | Zn 0.44-0.6 |
|---|---|---|---|---|---|---|---|---|
| 0.05 | 0.93 | 10.98 | 20.71 | 2.04 | 2.60 | 2.91 | 2.77 | 0.05 |
| 0.03 | 0.81 | 4.66 | 14.52 | 1.14 | 2.04 | 2.50 | 2.91 | 0.03 |
| 0.07 | 1.74 | 15.64 | 35.23 | 3.17 | 4.64 | 5.41 | 5.68 | 0.09 |
| 0.36 | 2.93 | 106.99 | 194.45 | 5.33 | * | 60.99 | 15.01 | 0.85 |
| 0.02 | 0.62 | 17.88 | 10.05 | 2.41 | 0.70 | 3.28 | 2.00 | 0.05 |
| 0.01 | 0.36 | 6.04 | 14.45 | 0.43 | 1.39 | 1.73 | 2.70 | 0.02 |
| 0.04 | 0.98 | 23.92 | 24.50 | 2.84 | 2.09 | 5.02 | 4.70 | 0.07 |
| 0.20 | 1.64 | 163.60 | 135.24 | 4.77 | * | 56.57 | 12.40 | 0.73 |

Fig. 22B

Slide 3

| Total Required Crop Nutrients: Yield Goal* (lb-req/unit of yield) | | | | | | | | | | |
|---|---|---|---|---|---|---|---|---|---|---|
| | Nitrogen (N) | Boron (B) | Calcium (Ca) | Copper (Cu) | Iron (Fe) | Magnesium (Mg) | Manganese (Mn) | Phosphate (P2O5) | Potassium (K2O) | Sulfur (S) | Zinc (Zn) |
| *1 | 1.1200 | 0.0027 | 0.1435 | 0.0008 | 0.0040 | 0.2333 | 0.0082 | 0.5100 | 1.3500 | 0.1500 | 0.0026 |
| *2 | 224.00 | 0.54 | 28.70 | 0.16 | 0.80 | 46.66 | 1.64 | 102.00 | 270.00 | 30.00 | 0.52 |

*1 Above: *Nutrient Requirements (lb/ac) per unit of yield*

*2 Above: *CORN*

*3 Above: *Nutrients (lb/ac) Required for 200 bu/ac*

Fig. 23A 200 bu/ac (yield goal) * 1.12 (lb/ac)/(bu/ac)(lb-req/unit of yield) = 224 lb/ac

*Fig. 23B*

| Table of Total Requirements (lb/ac) | | | | |
|---|---|---|---|---|
| Bushels/Acre | Alfalfa | Barley | Canola | CORN |
| Nitrogen (N) | 57 | 1.39 | 1.9 | 1.12 |
| Phosphate (P2O5) | 12.5 | 0.56 | 1.2 | 0.51 |
| Potassium (K2O) | 56 | 1.33 | 2 | 1.35 |
| Sulfur (S) | 5.5 | 0.175 | 0.34 | 0.15 |
| Magnesium (Mg) | 6.5 | 0.14 | 0 | 0.233297 |
| Calcium (Ca) | 31 | 0.227 | 0 | 0.1435 |
| Copper (Cu) | 0.015 | 0 | 0 | 0.000797 |
| Manganese (Mn) | 0.1 | 0 | 0.01 | 0.008203 |
| Zinc (Zn) | 0.05 | 0 | 0.01 | 0.002601 |
| Boron (B) | 0.065 | 0 | 0.01 | 0.002696 |
| Iron (Fe) | 0.30 | 0.00 | 0.02 | 0.004 |

*Fig. 23C*

224.0 lb/ac (Total N required from above)

− 117.40 lb/ac (Total N Available)

= 106.60 lb/ac (application prescription)

| Test | Target Range* | Total N | B | Ca | Cu | Fe |
|---|---|---|---|---|---|---|
| Total Rooting Profile Requirements (lb/ac): | | 190-258 | 0.46-0.62 | 24-33 | 0.14-0.18 | 0.68-0.92 |
| Zone 1 Test Total Sample Depth: 24" | | 117.40 | 2.03 | 216.43 | 0.36 | 2.93 |
| Application (lb/ac) | | 107 | −1 | −188 | 0 | −2 |
| Zone 2 Test Total Sample Depth: 24" | | 93.12 | 1.08 | 295.36 | 0.20 | 1.64 |
| Application (lb/ac) | | 131 | −1 | −267 | 0 | −1 |

| K (K2O) | Mg | Mn | P (P2O5) | S (SO4) |
|---|---|---|---|---|
| 230-311 | 40-54 | 1.39-1.89 | 87-117 | 26-35 |
| 106.99 | 194.45 | 5.33 | 60.99 | 15.01 |
| 163 | −148 | −4 | 41 | 15 |
| 163.60 | 135.24 | 4.77 | 56.57 | 12.40 |
| 106 | −89 | −3 | 45 | 18 |

Fig. 23D

| Zone Deficits (lb/ac): Nutrients Available- Nutrients Required | | | | | | |
|---|---|---|---|---|---|---|
| Zone 1: | Total N | NO3-N | NH4-N | Al | B | Ca |
| Total lb/ac available in profile: | 117.40 | * | * | * | 2.03 | 216.43 |
| Nutrients (lb/ac) required for 200 bu/ac: | 224.00 | * | * | * | 0.54 | 28.70 |
| Nutrient Deficit (lb/ac) for Zone: | -106.60 | * | * | * | 1.49 | 187.73 |

| Zone Applications (lb/ac): Nutrients Required- Nutrients Available | | | | | | |
|---|---|---|---|---|---|---|
| Zone 1: | Total N | NO3-N | NH4-N | Al | B | Ca |
| Total lb/ac available in profile: | 117.40 | * | * | * | 2.03 | 216.43 |
| Nutrients (lb/ac) required for 200 bu/ac: | 224.00 | * | * | * | 0.54 | 28.70 |
| Application Prescription (lb/ac) for Zone: | 106.60 | * | * | * | -1.49 | -187.73 |

| Cu | Fe | K (K2O) | Mg | Mn | Na | P (P2O5) | S (SO4) | Zn |
|---|---|---|---|---|---|---|---|---|
| 0.36 | 2.93 | 106.99 | 194.45 | 5.33 | * | 60.99 | 15.01 | 0.85 |
| 0.16 | 0.80 | 46.66 | 1.64 | 102.00 | * | 270.00 | 30.00 | 0.52 |
| 0.21 | 2.13 | 60.33 | 192.81 | -96.67 | * | -209.01 | -14.99 | 0.33 |

| Cu | Fe | K (K2O) | Mg | Mn | Na | P (P2O5) | S (SO4) | Zn |
|---|---|---|---|---|---|---|---|---|
| 0.36 | 2.93 | 106.99 | 194.45 | 5.33 | * | 60.99 | 15.01 | 0.85 |
| 0.16 | 0.80 | 46.66 | 1.64 | 102.00 | * | 270.00 | 30.00 | 0.52 |
| -0.21 | -2.13 | -60.33 | -192.81 | 96.67 | * | 209.01 | 14.99 | -0.33 |

Fig. 24B

Sample Application Prescription Report (lb/ac)

| Test | Target Range* | Total N | B | Ca | Cu | Fe | K (K2O) |
|---|---|---|---|---|---|---|---|
| Total Rooting Profile Requirements (lb/ac): | | 190-258 | 0.46-0.62 | 24-33 | 0.14-0.18 | 0.68-0.92 | 230-311 |
| Test Zone 1 | | 117.40 | 2.03 | 216.43 | 0.36 | 2.93 | 106.99 |
| Total Sample Depth: 24" Application (lb/ac): | | 107 | -1 | -188 | 0 | -2 | 163 |
| Test Zone 2 | | 93.12 | 1.08 | 295.36 | 0.20 | 1.64 | 163.60 |
| Total Sample Depth: 24" Application (lb/ac): | | 131 | -1 | -267 | 0 | -1 | 106 |

| Mg | Mn | P (P2O5) | S (SO4) | Zn |
|---|---|---|---|---|
| 40-54 | 1.39-1.89 | 87-117 | 26-35 | 0.44-0.6 |
| 194.45 | 5.33 | 60.99 | 15.01 | 0.85 |
| -148 | -4 | 41 | 15 | 0 |
| 135.24 | 4.77 | 56.57 | 12.40 | 0.73 |
| -89 | -3 | 45 | 18 | 0 |

Fig. 25B

METHODS AND APPARATUS FOR DETERMINING FERTILIZER/TREATMENT REQUIREMENTS AND/OR PREDICTING PLANT GROWTH RESPONSE

This application claims benefit of U.S. Provisional applications, Ser. No. 62/127,115, filed Mar. 2, 2015, Ser. No. 62/127,146, filed Mar. 2, 2015, and Ser. No. 62/127,181, filed Mar. 2, 2015, all of which provisional applications are incorporated herein by this reference.

BACKGROUND

Field of the Technology

The field of this technology is: METHODS AND APPARATUS FOR DETERMINING FERTILIZER/TREATMENT REQUIREMENTS AND/OR PREDICTING PLANT GROWTH RESPONSE, and/or REPORTING METHODS FOR THE SAME OR SIMILAR DATA AND RECOMMENDATIONS. More specifically, the methods and/or apparatus relate to sampling and testing methods, and/or fertilizer/treatment application methods, for improving plant growth, crop yield, fertilizer and/or chemical usage, timing, and/or economy, and/or environmentally-conscious land and/or agricultural business management.

SUMMARY

Testing of one or more soil samples, and/or in-situ testing in the soil(s), is done to determine one or more "available nutrient" levels, that is the amount(s) of nutrient(s) that are available to a plant during growth in that soil(s). As explained later in this document, the nutrients "available" to a plant are analyzed in the preferred embodiments by apparatus and methods that analyze/measure amounts of nutrients that would, in the field, actually be available to the plant root for uptake by the living and growing plant, rather than simply the total nutrient in the soil including the nutrient bound to/in the soil that is unlikely to leave the soil to enter the plant root. Therefore, the "available" nutrient may be, and typically is, different from the total nutrient in the soil, for example, as measured by conventional chemical analysis of the soil, due to differences and idiosyncratic characteristics of each soil regarding how much (and the timing of) release of the nutrient from, and flow of the nutrient through, the soil to the plant root, for example, via water/moisture that carries the nutrient released from the soil to the plant root in a way that can be taken-up by the plant root.

In certain embodiments, soil samples are mixed with water to form a slurry, and then the slurry is tested according to the disclosed methods, so that the variable of soil moisture content may be lessened or eliminated from consideration. In certain embodiments, even with substantial water available in the slurry to carry nutrients through the soil and to the sampling device, the "available nutrients" are significantly less than, the total nutrients in the soil (due to binding and/or other mass transfer limitations within the soil). Field moist soils, in certain embodiments, can be directly added to deionized water in a vial, either at the point of sample location or later on in the lab.

While "slurry" is used herein, for cases where a lot of water is added to the soil, also "soil paste solutions" may also be used in the baseline analysis or the later (fertilizer-added analyses). This way, results can be compared without the concern for moisture variability in the field for non-irrigated crops.

An "initial available nutrient" is determined from the soil sample, in slurry form, and without any added nutrients (without any fertilizers or treatment chemicals added at the lab). This determination is compared/correlated to nutrient requirements for desired plant growth during one or more periods of time, and/or to a yield outcome desired, for example, by comparison of the initial available nutrient to a database or other tabulation that correlates needed nutrients with plant growth and/or yields. For example, said database/tabulation may be the known IPNI™ database/system for correlating what total nutrients over a grow season are required to accomplish a given target crop yield. The comparison/correlation may be done for specific selected nutrients, and/or to specific selected plants/crops and/or for specific selected target yields. The comparison/correlation may be used to predict the type, composition, and quantity of fertilizer or other treatments to be applied to the soil(s) in which the plant/crop is being grown or will be grown.

The testing of said soil samples, or said in-situ testing, is particularly important due to soils being different and/or unique in their properties and especially in their characteristics regarding nutrient availability to a plant growing in that soil. For example, different soils will exhibit different release of nutrients to water in the soil and/or will otherwise exhibit different rates and/or location/depth profiles of making nutrients available to the plant roots. Further, said testing of samples from, or in-situ testing in, different depths below the soil top surface is important in many embodiments, preferably through the entire root zone for a selected plant species.

"Initially available" to a plant may mean before the growing season, and/or at any time desired, to obtain a base-line nutrient level for the soil, against which to compare what may be needed to remediate or improve the soil and/or to determine trends over time in the soil. This term means, in certain embodiments, before fertilizer is added, for example in the fall or winter or early spring before planting. Or, in other embodiments, the testing may be done at the same time every year, when the agriculturist or other manager (hereafter, "manager"), or the analyst or consultant judges that the soil sample/testing will be indicative of the generally steady-state or current character/composition of the soil, or any desired time.

In preferred embodiments, after the initial testing, fertilizer(s) or other treatment composition(s) are added to other portions of the same soil sample(s) that were initially tested. The fertilizer/treatment is added in different amounts to portions of the soil, is mixed/shaken, and then allowed to rest for an amount of time. This amount of time may be, for example, several hours or several days (for example, five days, seven days, or more preferably one or two days). These varying amounts may be, for example, fractions of a "full amount" that is calculated and/or estimated to be the amount needed to reach the nutrient level in the soil necessary for the target plant growth/yield. For example, the soil may be divided into multiple sub-samples, and each of the sub-samples may be treated with different amounts of fertilizer/treatment composition. For example, one sub-sample may be treated with 25%, another with 50%, another 75%, and another 100%, of the "full amount" of fertilizer/treatment composition. In such a case, therefore, the original soil sample provided from the field/land may be divided or managed so that at least 5 very similar or identical sub-samples are available for the total testing program, that is, one sub-sample for the initial (base-line) testing, and four sub-samples for the different amounts of fertilizer/treatment composition.

Then, each of the treated sub-samples is analyzed for available nutrient levels, preferably by methods and apparatus that, as mentioned above and detailed below, or, as will be understood from the following discussion, preferably the nutrients levels that would be available to the plant root growing in the treated soil, rather than the total nutrient in the sample.

The testing procedures are preferably done with resin sampler apparatus, in the lab, wherein a slurry of water and a sub-sample of soil is placed in contact with the resin sampler. This way, the resin sampler adsorbs nutrients much as a plant root would, so that the resin is like "an artificial or substitute plant root" acting picking up nutrients similarly to a plant root, to replicate, mimic, or approximately the environment of nutrients actually available to the plant. For teachings of the resin samplers of most interest, see Ser. No. 14/321,380 filed Jul. 1, 2014, now U.S. Pat. No. 9,709,471, by Riess and Crass, wherein this non-provisional application, its parent non-provisional Ser. No. 13/227,445, now U.S. Pat. No. 8,763,478, and the earlier provisional Ser. No. 61/380,320 that the parent claims benefit of, are incorporated herein by this reference. In certain embodiments, the resin samplers in this incorporated document, or similar resin holding devices are inserted into, or otherwise contacted in the lab with the slurry to be tested, rather than inserting the resin sampler into the field in-situ. Resin samplers may comprise a screen of various mesh/opening sizes, but typically the screen mesh sizes are the nominal range of 100 to 500 micron openings, with a preferred opening size being in the range of 200-300, or about microns. Within the preferred range of 100-500 micron screen openings, the screen opening size may be chosen for different resins and different soils and/or water, to provide minimal infiltration of soil into the sampler, for example. The screen allows fluid, and, in certain embodiments small particles of soil and sand and other solids to infiltrate into the sampler to reach the resin/adsorbent, but prevents larger materials such as rocks, pebbles, and sticks to reach the resin/adsorbent. Alternative resin sampling containers may be used, for example, spherical capsules or other containers, as long as there is excellent contact between the slurry and the resin. Currently over 900+ types of resins manufactured worldwide. Strong or weak resins are specifically selected for their affinity to attract cations and anions of concern. Loose, granular ion-exchange resin may be contained in the resin sampler containers. There is a unique science associated with the selection and blends of resins that can be created to target groups of contaminants, and more preferably subsets of or individual contaminants, of concern.

After multiple, different fertilizer/treatment applications on the multiple soil sub-samples, and determining the effect of each application on the available nutrients (again, as measured by the "artificial root" in the form of resin sampler"), the analyze/advisor may provide the "available nutrients" for various levels of fertilizer/treatment application to the client's particular soil. The result may be surprising, in that a smaller fertilizer/treatment application than predicted by conventional data (such as IPNI) may actually be sufficient or beneficial, because these methods take into account the unique properties/behavior of the particular soil. Or, on the other hand, the result may be surprising, in that a larger fertilizer/treatment application than predicted by conventional data (such as IPNI) may actually be needed to make sufficient or desired nutrients available to the resin sampler (and therefore the plant root), again because of the unique properties/behavior of the particular soil.

In alternative embodiments, reporting is done according to improved tables and graphics that show the client the baseline, incremental effect on preferably multiple (for example, 14) nutrients, of added fertilizer and/or other chemical treatments, per the methods described herein. The reporting may include correlations to plant growth, tissue samples and/or composition, and other data such as climate, precipitations, etc., as disclosed in the Figures and later in this document.

In alternative embodiments, invented apparatus is provided for quick, convenient, accurate, and high quality handling, filling, cleaning, and/or leaching steps of the resin samplers, for example, for the analytical and/or reporting according to the desired methods herein or for other lab or testing methods. For example, apparatus is provided for filling of resin samplers, such as the preferred cylinder samples (as in Ser. No. 14/321,380, now U.S. Pat. No. 9,709,471), or capsules, or other sampler devices that provide a great amount of contact between the resin and the medium/material to be tested: for example, A) the water and soil slurry, or B) the slurry of water, soil, and added fertilizer/treatment composition. In alternative embodiments, apparatus is provided for cleaning and/or leaching of the resin samplers, for example, the preferred cylinder samples (as in Ser. No. 14/321,380, now U.S. Pat. No. 9,709,471), or capsules, or said other sampler devices. One may understand from this disclosure, and Ser. No. 14/321, 380, now U.S. Pat. No. 9,709,471 that the samplers will be removed from, and/or cleaned of, the slurry/paste they are immersed/contacted-with, and then a leaching process is conducted to determine what nutrients or other chemicals have been adsorbed onto the resin during the test period, in other words, the nutrients or other chemicals that adsorbed onto the resin, indicating the type and amounts of nutrients/chemical "available to the resin" and, hence, "available to the root". As mentioned above, samples may be taken and analyzed from multiple soil depths, preferably, the entire "root zone" for a given crop.

The apparatus, in certain embodiments, may be used manually, or, in other embodiments, automatically. The apparatus is specially-designed for rapid and highly-uniform and proper handling, filling, cleaning and/or leaching, of the many samplers that will typically be involved in testing, for example, for many clients, for large tracts of land or many sub-regions or soil depths, within a tract of land.

See the following examples of some, but not the only, embodiments of the invented methods and/or apparatus. Note that UNIBEST™ used herein or in the figures is a trademark owned by UNIBEST INTERNATIONAL, LLC., WALLA WALLA, WASHINGTON 99362.

BRIEF DESCRIPTION OF THE DRAWINGS

FIGS. 1-7 are schematics illustrating a TRY BEFORE YOU APPLY™ process of Example 1, wherein:

FIG. 1 is a schematic of soil being extracted from a desired depth(s) within a soil profile using an auger.

FIG. 2 is a schematic of a sample being transferred to a container to maintain moisture content.

FIG. 3 is a schematic of sample tracking/login and accessing sample information/ID via computer.

FIG. 5 is a schematic of sample results determined by the UNIBEST method being used for reporting of baseline nutrients and recommending fertilizer trials.

FIG. 7 is a schematic of results from fertilizer trials being used for fertilizer application recommendations.

FIGS. 8-19 illustrate an example of plant response prediction as in Example 2, wherein:

FIG. 8 (split onto two sheets as FIG. 8A and FIG. 8B) gives an example of a data report that summarizes nutrient deficits for multiple locations on a farm.

FIG. 9 shows an example of a sustainability report.

FIG. 10 (split onto two sheets as FIG. 10A and FIG. 10B) shows an example of a TRY BEFORE YOU APPLY™ Fertilizer Application Recommendation Report.

FIG. 11 depicts a variable rate map layer using UNIBEST ion exchange resin data and UNIBEST algorithms.

FIG. 12 (split onto two sheets as FIG. 12A and FIG. 12B) depicts a variable rate map layer displaying a recommended nutrient application generated using UNIBEST Ion exchange resin data coupled with UNIBEST algorithms on a variable rate mapping system.

FIG. 13 depicts resin to tissue testing correlations between various growth stages.

FIG. 14 shows examples of graphs which demonstrate a correlation between soil nutrient concentration measured by resins and nutrient concentration in plant tissue.

FIG. 15 is a graphic of profile nutrient availability modeling.

FIG. 16 gives an example algorithm for calculating nutrient deficit, as well as a general formula that may be used for nutrient deficits or other concentration deviations.

FIG. 17 shows an example of an equation that may be used to calculate fertilizer application rate, as well as the general form of an algorithm used for procedural amendments.

FIG. 18 shows an example of an algorithm that may be used to predict soil response to fertilizer application, as well as the general form of an algorithm for predicted outcomes.

FIG. 19 shows an overview of Resin-to-Tissue based analytics.

FIG. 20, FIG. 21 (split onto two sheets as FIGS. 21A and 21B), FIG. 22 (split onto two sheets as FIGS. 22A and 22B), FIGS. 23A-D, FIGS. 24A and B, and FIGS. 25A and B) illustrate reporting and advising methods of Example 3, wherein:

FIG. 20 illustrates methods wherein UNIBEST resin analysis leads to zone application prescription (lb/ac).

FIGS. 21A and B illustrate data from the analysis of FIG. 20.

FIGS. 22A and 22B illustrate a Sample Report of Available Nutrients.

FIG. 23A illustrates a report of Total Required Crop Nutrients.

FIG. 23B illustrates a formula for determining pounds/acre (lb/ac).

FIG. 23C illustrates a report of Table of total Requirements (lb/ac).

FIG. 23D illustrates a report of application prescriptions and a calculation of application prescription for nitrogen listed therein for Zone 1.

FIG. 24B illustrates reporting of Zone Deficits and Zone Applications.

FIG. 25B illustrates a Sample Application Prescription Report (lb/ac) for Total N, B, Ca, Cu, Fe, K(K2O), Mg, Mn, P(P205), S(SO4), and N, for two zones.

FIGS. 27, 28A-D, 29A and B, 30, 31A and B, 32, 33, and 34A and B, are schematic illustrations of apparatus/methods of a manual cylinder filing station of Example 5, wherein:

FIG. 27 a schematic side view of an automatic cylinder filling system.

FIGS. 28A-D schematically illustrate details of the automatic cylinder filling system, wherein conveyor belt(s) is/are used to move cylinder holding devices from station to station.

FIG. 29A and FIG. 29B schematically illustrate details of the automatic cylinder filling system, wherein empty cylinders may be loaded into a hopper and then loaded into a holding device.

FIGS. 35-39 schematically illustrate an automatic cleaning system/station for capsule(s)/cylinder(s) of Example 6, wherein:

FIGS. 35 and 36 are a perspective view, and a close-up detail view, respectively, of the automatic cleaning system/station holding capsules.

FIG. 37 is a close-up detail view of the automatic cleaning system/station holding capsules.

FIG. 38 schematically illustrates a tray designed to hold capsules directly under directional jets of the automatic cleaning system/station.

FIG. 39 schematically illustrates a tray designed to hold cylinders directly under directional jets of the automatic cleaning system/station.

FIGS. 40-47 illustrate an automatic leaching system/station for capsule(s)/cylinder(s) of Example 7, wherein:

FIG. 40 is a perspective view of the automatic leaching system/station holding capsules.

FIG. 41 is a perspective view of the automatic leaching system/station holding cylinders.

FIG. 42 is a close-up detail of the automatic leaching system/station holding capsules, wherein emitters are placed so that the leaching agent is distributed directly over the center of capsules to ensure even distribution.

FIG. 43 is a close-up detail of the automatic leaching system/station holding cylinders, wherein emitters are placed so that the leaching agent is distributed directly over the center of cylinder to ensure even distribution.

FIGS. 44 and 45 illustrate funnels of the automatic leaching system/station.

FIGS. 46 and 47 illustrate a tray designed to hold capsules, and a tray to hold cylinders, respectively, of the automatic leaching system/station.

DETAILED DESCRIPTION OF CERTAIN EMBODIMENTS

Example 1

An Example of a Try Before You Apply™ Process

Matching fertilizer application rates to plant/crop needs is an essential component of maximizing crop production for precision agriculture. However, different plants/crops require varying rates of nutrients. Precisely determining these rates can be quantified and optimized to predict yield goal, increase plant health, and reduce excess environmentally sensitive nutrients.

Step 1: Sample Preparation

Figure 1:
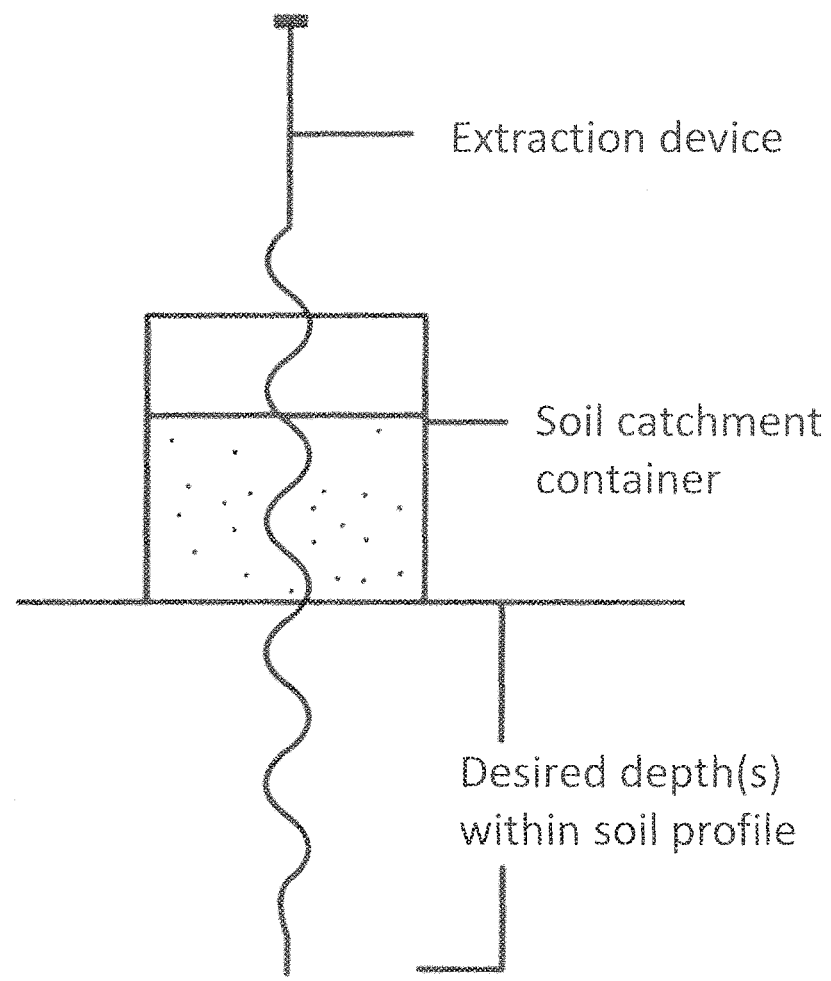

UNIBEST Resin systems are placed in, surrounded, or encompassed with testing medium, either in-situ or paste composite. Paste composite is composed of field moist soils extracted from desired depths using mechanized auger, drill, or similar, which finely mixes and equally distributes soil particles. Composited samples are collected in catchment container, bucket, or enclosure. See FIG. 1.

Step 2: Sample Tracking

Figure 2:
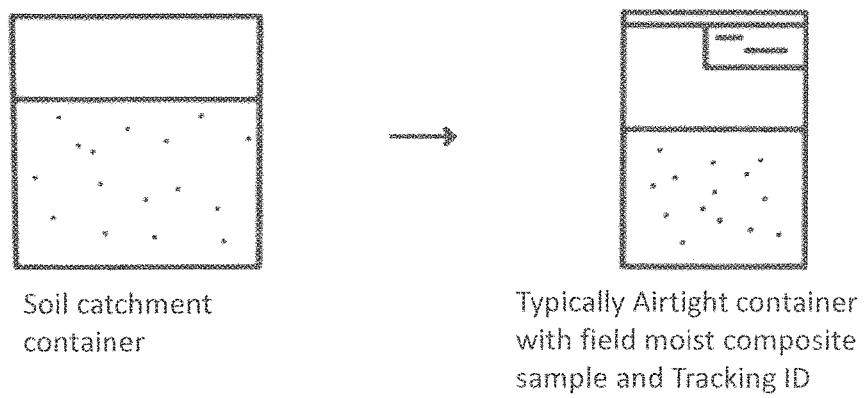

Samples are transferred into container to maintain moisture content. See FIG. 2.

Samples are sorted, organized, grouped, and labeled for location, depth, time, and season. Furthermore, samples are logged into computer data base and referenced/combined with but not limited to listed variables:

1. UNIBEST Resin Data Parameters: Ppm, Sample depth, In-situ vs paste, Capsule vs. cylinder, Ratios of soil variables (i.e. N to P ratio).
2. Soil/seed Parameters: pH, Soil type/soil class, CEC, Bulk density, Moisture, seed genetics, Plant/Crop type, Growth stage, Organic matter, Percent humic matter, Root zone profiling/horizonation, Conductivity, Heavy metals, Soil air, Consistence, Solubility, Dissolved gases, Percent base saturation, Weight-to-volume ratio, Soil Color, Soil Compaction, Soil Structure, Soil Texture, Other nutrient tests (i.e. a nutrient we don't test like Cl), Projected yield/yield goal, Previous yield, seed depth, Herbicides, Pesticides, Plant density.
3. Geospatial Models and Variables: Climate models, Temperature, Rainfall, Sun, Season, frozen, Satellite Crop Modeling/remote sensing data/UAV, NDVI, XRF, Chlorophyll index, Ultraviolet florescence, Topography/slope/aspect, land classification, Geostatistics.
4. Agricultural Practices Variables: Tillage Practices (Reduced, intensive, conservation (no till, strip till, mulch till, rotational tillage, ridge till, zone tillage), Cover crops, Application Method (Fertilizer type, Liquid/solid, Application timing/frequency), Past land uses, Irrigation technique, Seeding/Harvesting timing, Crop rotation/crop variability, Conservation techniques (i.e. soil drainage/tile drainage), Manure analysis, Compost analysis, Projected yield/yield goal, Previous yield, Seed depth, Herbicides, Pesticides, Plant density.
5. Other: Multivariate models (combine variables, such as tillage and moisture), Forestry (Satellite data/remote sensors, Live tree basal area, Canopy cover), Hydroponics (Nutrient solution, Technique (Wick, Water Culture, Nutrient Film Technique, Drip, Solution culture (Static, Continuous flow, Aeroponics, Passive sub-irrigation, Ebb and flow/flood and drain sub-irrigation, Run to waste, Deep water, Top-fed deep water, Fogponics, Rotary), medium culture (substrate type/medium)).
6. Databases: IPNI, Plant genetic databases.
7. Algorithms/Modeling: Nutrient Deficiency, Fertilizer Application rate, Watering rates, Variable rate modeling, Nutrient Loss/Use modeling.
8. Prediction Goals: Management goals (Crop yield, Maintenance goals (i.e. turf color, plant size), Quality goals (i.e. grape quality, plant nutrient levels)), Sustainability modeling/environmental impacts.

Step 3: Sample Tracking

Figure 3:
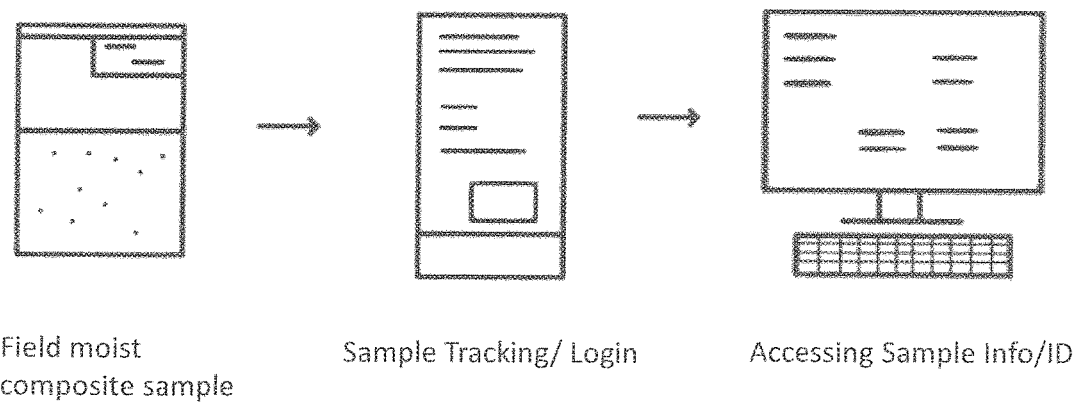

Soil sample tracking/login can be completed on paper, smart phone, cell phone, tablet, handheld computational device, laptop, desktop, or computer through application (app), program, file, or software. Sample identification can be tracked, accessed, searched for, and databased through/using barcode and industry standard barcodes, numerical value, alpha-numeric, and/or alphabetical. Sample database can be accessed for testing in combination with UNIBEST laboratory method. See FIG. 3.

Step 4: Sample Distribution

Figure 4A:
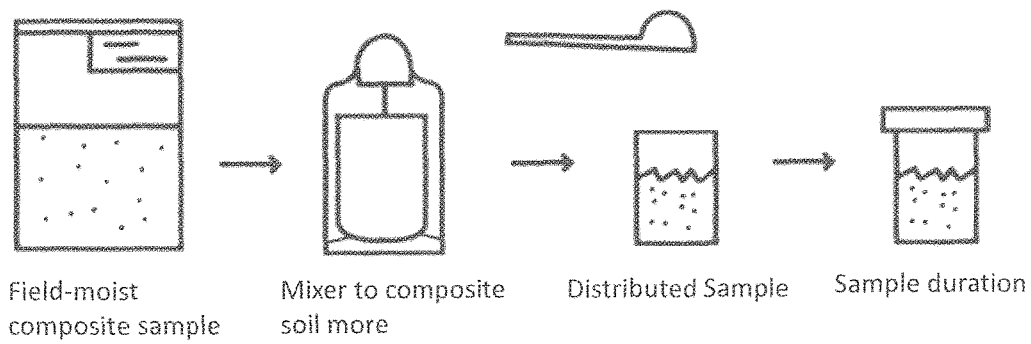
FIG. 4A is a schematic of a sample distribution process, including steps of mixing a field-moist composite sample to composite the soil more, distributing the sample, and sample duration, for processing according to the UNIBEST method to achieve baseline nutrient levels.
Figure 4B:
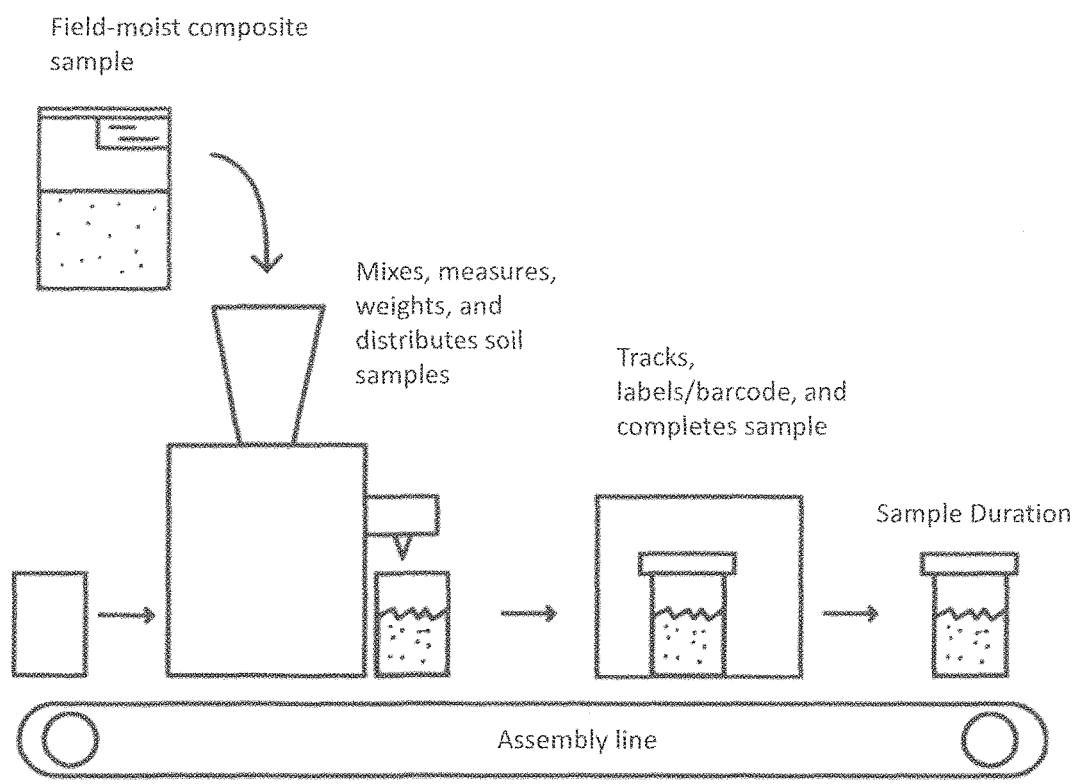
FIG. 4B is a schematic of a high throughput sample distribution.

Testing samples are distributed to quantified amounts (weight or volume) and tested using ion-exchange resin. Distribution of testing medium can be accomplished manually by personnel but not limited to fully automated computerized systems, or within remote sensing platforms. Testing medium is administered into testing container, jar, vile, cup, or beaker. Medium can be tracked, accessed, searched for, and databased through/using barcode and industry standard barcodes, numerical value, alpha-numeric, and/or alphabetical. Testing medium goes through sample duration and is processed according to the UNIBEST method to achieve baseline nutrient levels. See FIG. 4A. For a schematic illustration of high throughput sample distribution, see FIG. 4B.

Step 5: Baseline Nutrient Results, Fertilizer Trial(s)

Figure 5:
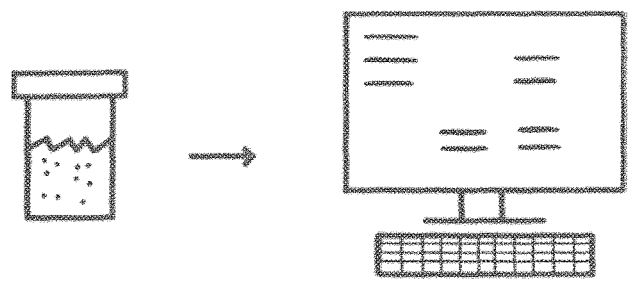

Once baseline nutrient levels are determined through resin analysis using the UNIBEST method, specific algorithms are computed with variables to determine fertilizer trials. Multiple trial recommendations can be given. Fertilizer trials are tested within customer/growers field-most soils in laboratory settings. See FIG. 5.

Step 6: Fertilizer Trial(s)

Figure 6A:
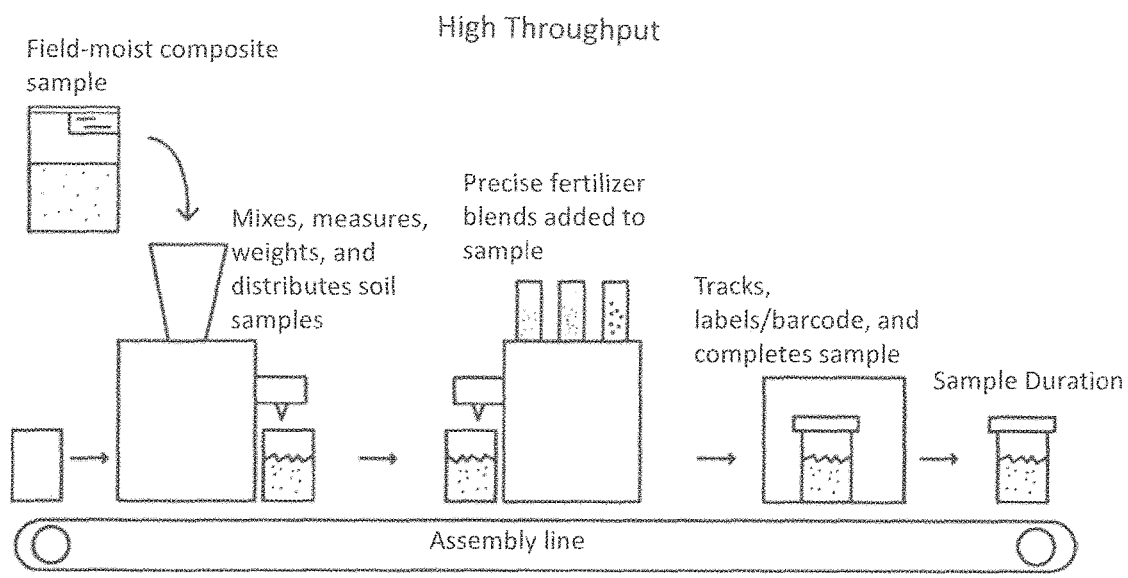
FIG. 6A is a schematic of a high throughput process for fertilizer trials.
Figure 6B:
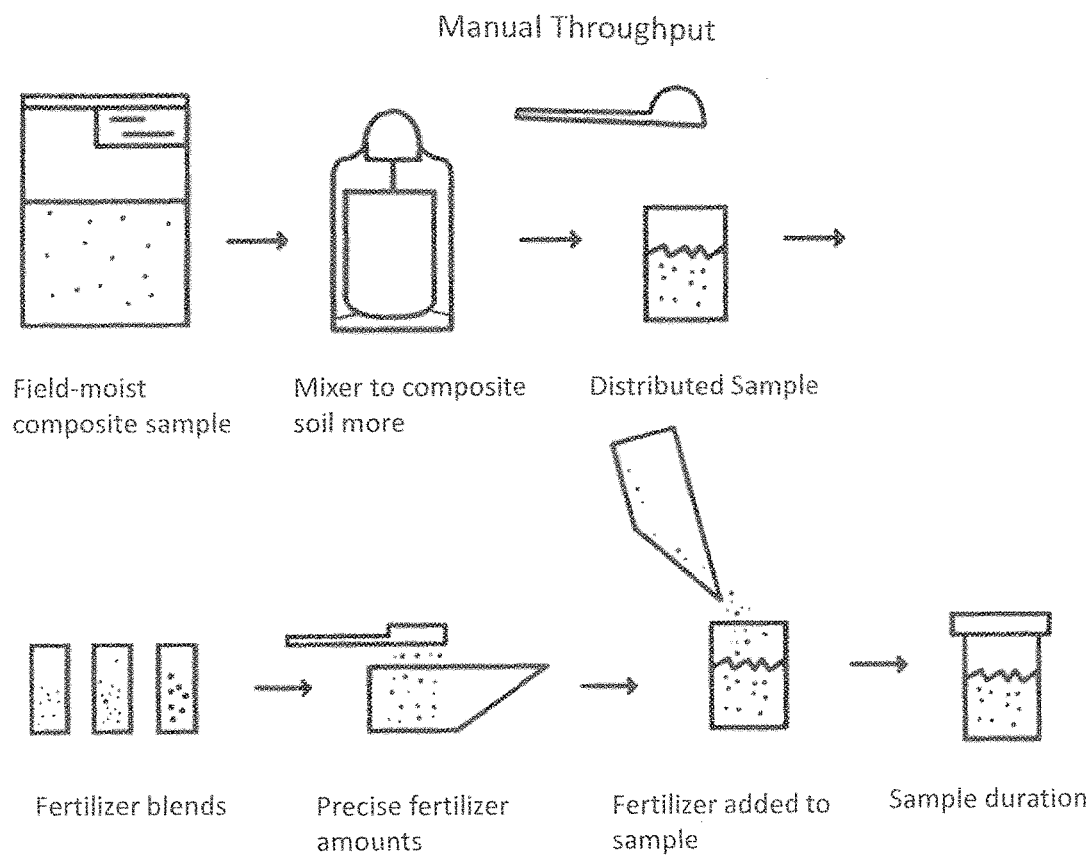
FIG. 6B is a schematic of a manual throughput process for fertilizer trials.

Precise fertilizer trials are administered following the same procedure manually, automatically, or remotely in Step 4 for sample distribution. Precise amounts of fertilizer(s) can be controlled through manual dispensing, remote sensing platforms, micro-dispensing pumps, scales (micrograms), or automatic micro measuring devices for liquid, powder, granular, chelated, or ground substances. Fertilizer can be added before or after soil distribution. Trials are tracked, accessed, searched for, and databased through/using barcode and industry standard barcodes, numerical value, alpha-numeric, and/or alphabetical. Trials are processed according to the UNIBEST method. See the high throughput example in FIG. 6A. For a schematic illustration of a manual throughput trial, see FIG. 6B.

Step 7: Fertilizer Application Recommendation(s)

Tested results will be formatted for but not limited to customers, growers, agronomists, farmers, precision Ag tools, and GIS programs, allowing for the application of precise fertilizers to plant/crop. Results show how fertilizer trials perform within field-moist soils. Best results will be used for application recommendation.

Figure 7:
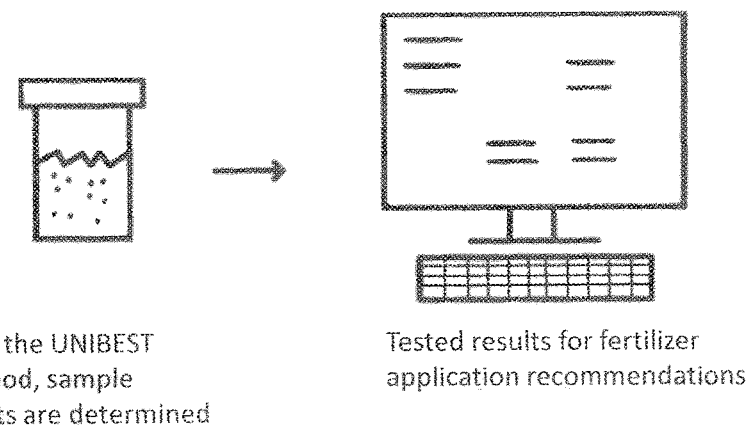

Precise fertilizer recommendations can save time and money on inaccurate field applications, either over or under applying, and yield loss due to malnutrition. Yield, deficiencies, depravation, and surpluses can be predicted prior to planting. Minimization of off-target movement of environmentally sensitive nutrients can be achieved by applying the right fertilizer at the right rate, at the right time, and in the right place. See FIG. 7.

Example 2

An Example of Plant Response Prediction

UNIBEST resin systems are proven to be predict plant response. Prediction of plant response generates a data set specific to UNIBEST resin systems with a variety of uses and applications. Each application or use follows the UNIBEST resin system from sample collection to data acquisition. Each step is specific to UNIBEST and requires specific algorithms and processes to produce data applicable to practical use. These processes and algorithms have been developed by UNIBEST and are specific to UNIBEST systems. UNIBEST algorithms and processes produce data sets for a variety of uses that include but are not limited to precision agriculture, variable rate mapping, golf & turf, professional landscape and home lawn and garden.

FIG. 8 gives an example of a data report that summarizes nutrient deficits for multiple locations on a farm. Nutrient deficits are based on resin measurements of the nutrients available for plant uptake, and crop nutrient requirements (specific to relevant parameters such as crop type, growth stage and sample depth). Resin measurements of the nutrients available for plant uptake are correlated with plant tissue needs and produce accurate estimates of nutrient deficits in soil and how much of each nutrient must be added to maximize crop yield. Other data reports may recommend fertilizer application rates or other management practices, predict yield or other management objectives, evaluate sustainability and/or environmental impacts, provide "Try Before You Apply" fertilizer application procedures, be used in variable rate mapping, be incorporated into other technology platforms, or report other important agricultural information.

Figure 9:
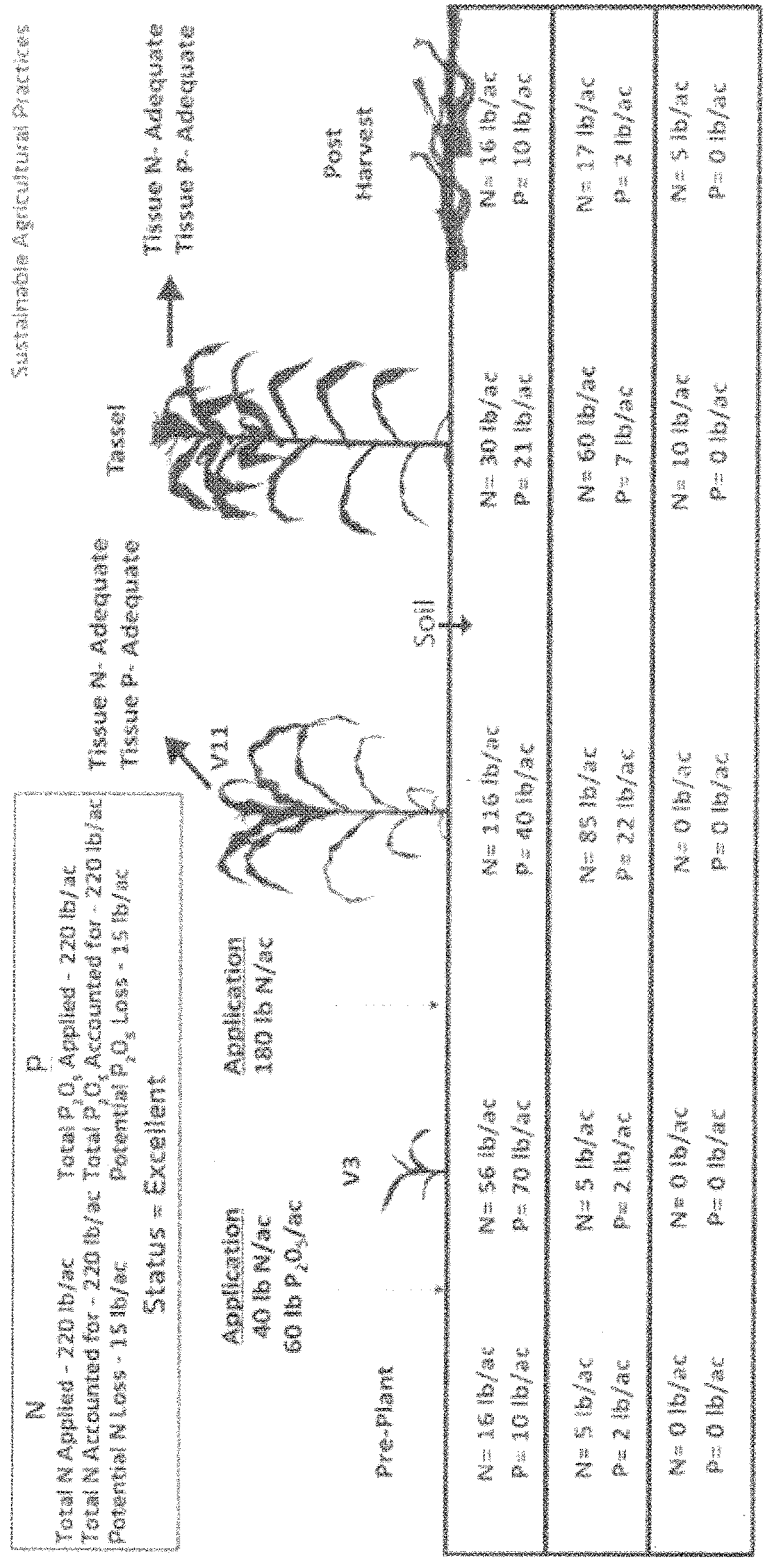

FIG. 9 shows an example of a sustainability report. Resin analysis may be used for evaluation of Best Management Practices, Natural Resource Damage Assessments, and other reports of sustainable practices, environmental outputs or other quantities that may be important to sustainable agriculture and the environment.

FIG. 10 gives an example of a "Try Before You Apply" Report, which may consist of key summaries such as an initial soil evaluation, laboratory trial results, recommendations, and other important parameters/summaries of soil data. An initial summary is a soil evaluation which acts as a baseline and may include nutrient deficits or other important summaries of crop needs. Laboratory trial results are a summary of how the soil and/or plant needs respond to one or multiple fertilizer application procedures, which may vary key factors such as fertilizer application rate, fertilizer type/brand, form (solid/liquid) and application timing. Recommendations for fertilizer application procedures are based on the results of the laboratory trials, and preferably also based on one or multiple other important parameters such as climate models, tillage practices, environmental impact models or other parameters important to fertilizer application.

Figure 11:
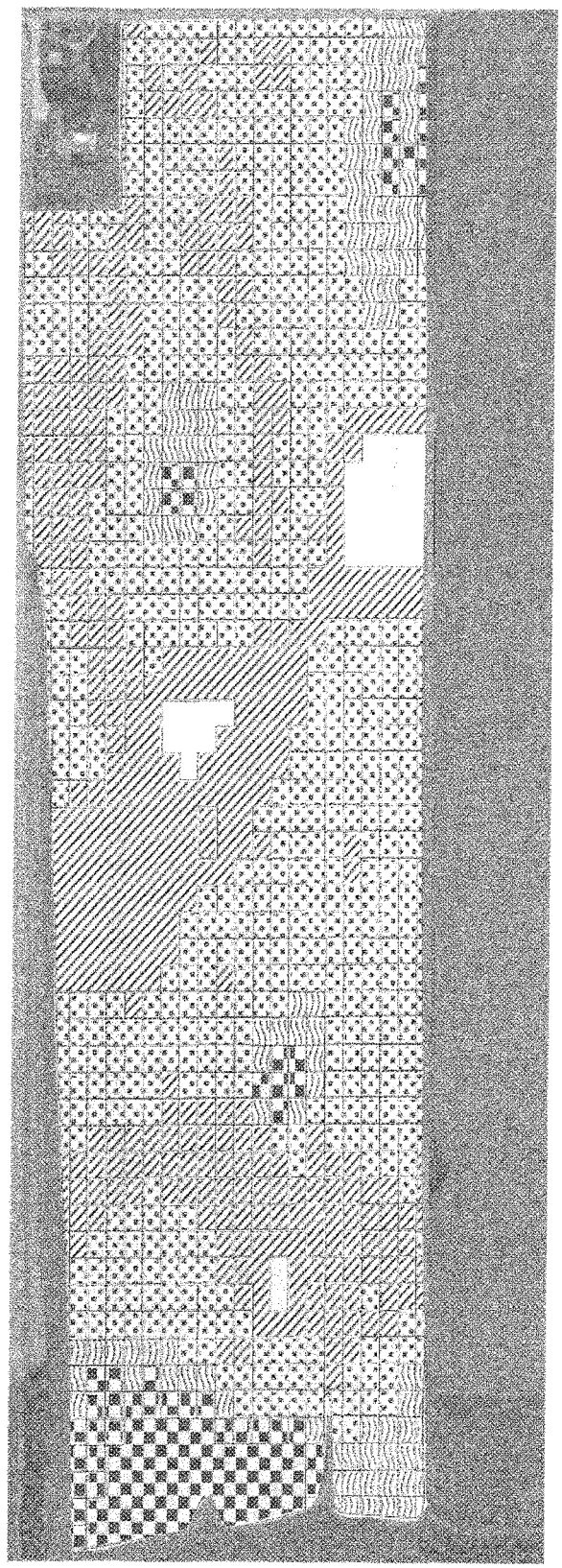

FIG. 11 depicts a variable rate map layer using UNIBEST ion exchange resin data and UNIBEST algorithms. Algorithms used can vary based on a variety of parameters and/or layers available within the variable rate mapping system. The parameters can be, but are not limited to, climatic variables, profile sampling techniques, soil properties and characteristics, nutrient application techniques, and variable rate mapping programs.

Figure 12A:
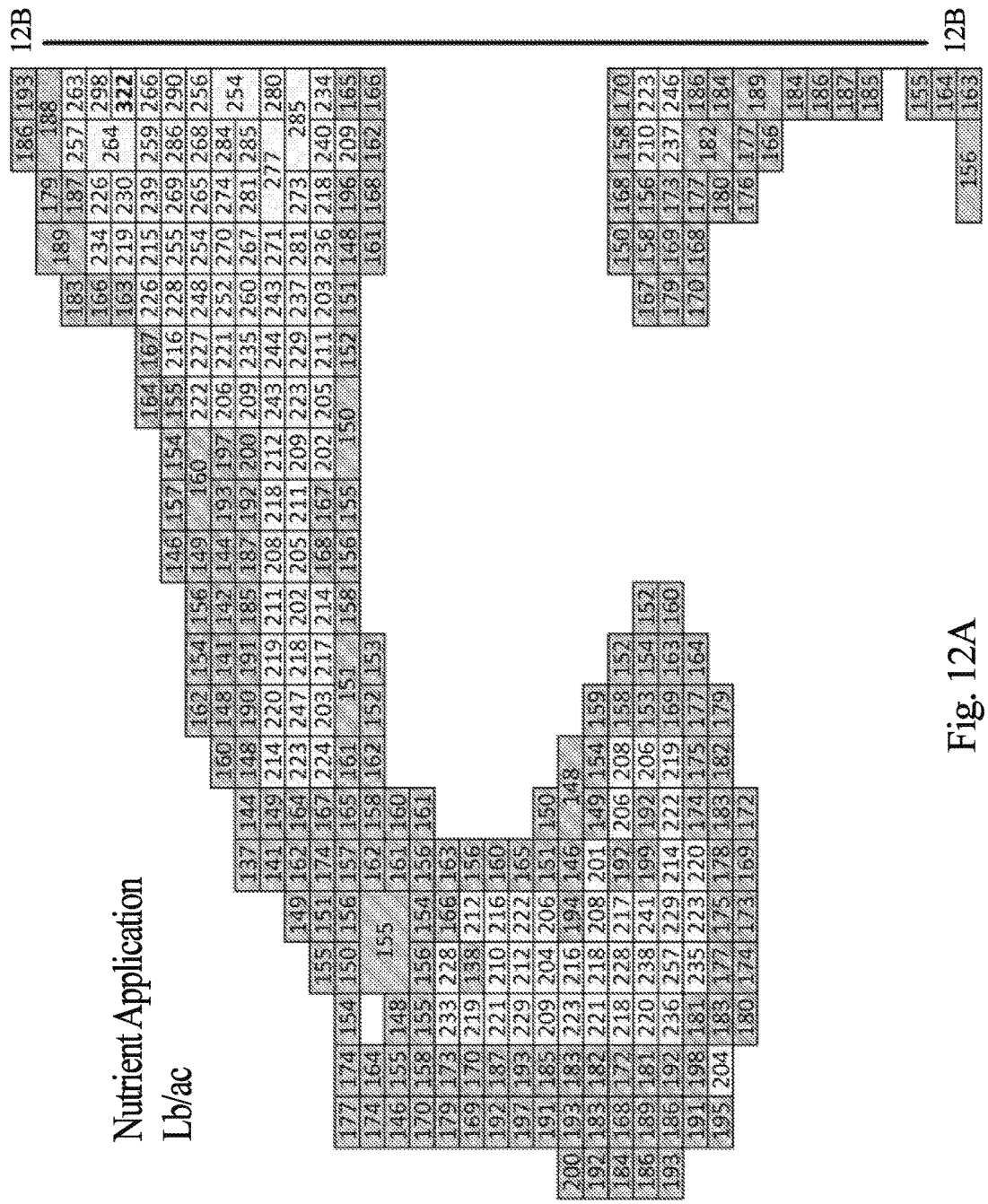

FIG. 12 depicts a variable rate map layer displaying a recommended nutrient application generated using UNIBEST Ion exchange resin data coupled with UNIBEST algorithms on a variable rate mapping system. It is easily adopted into a variety of compatible variable rate mapping systems including, but is not limited to, ArcGIS©, SST©, R7® Tool.

Figure 13:
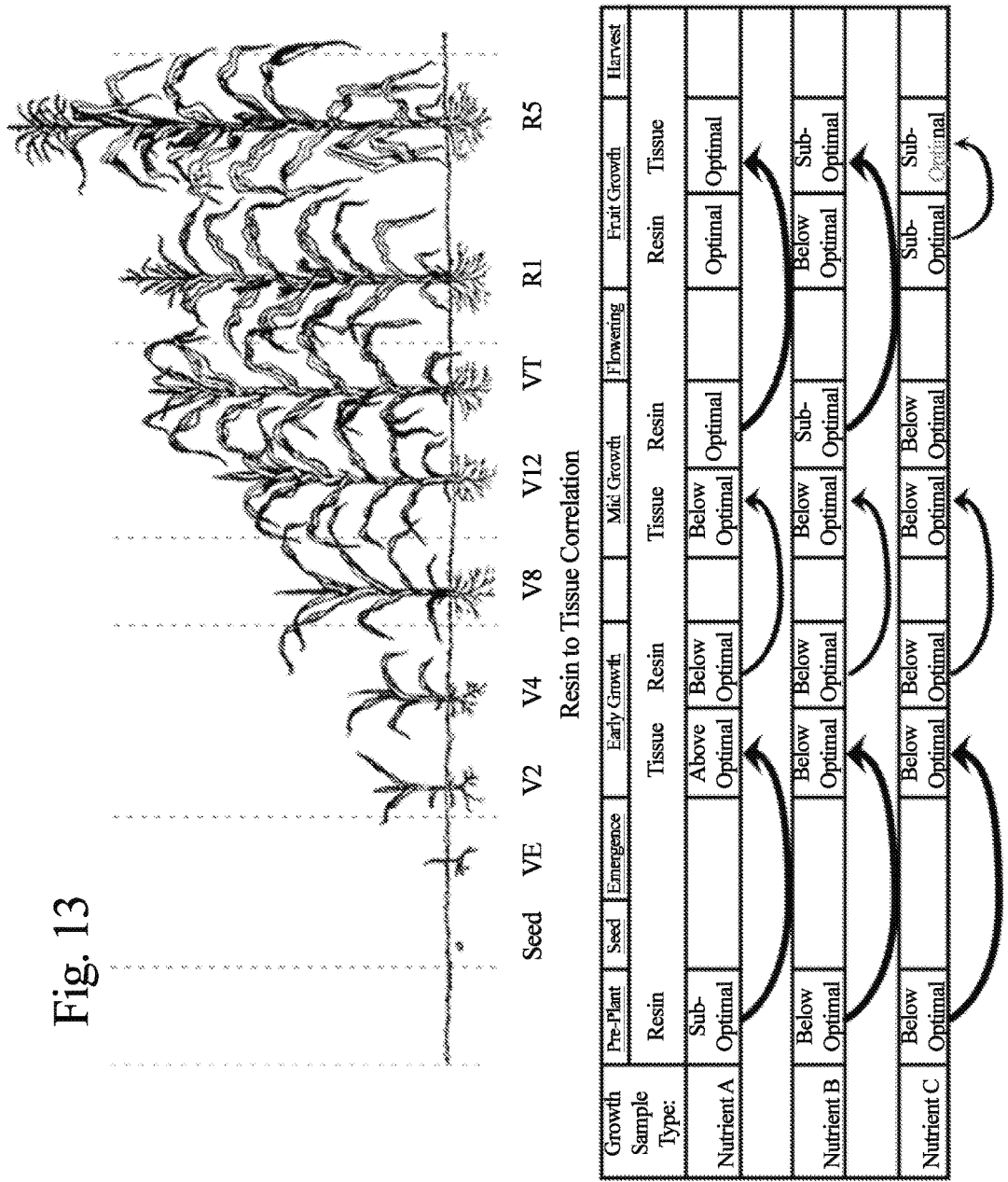

FIG. 13 depicts resin to tissue testing correlations between various growth stages. Resin testing can predict potential plant nutrient deficiencies prior to occurrence in healthy plants, permitting time for soil nutrient corrections. Proper resin to tissue correlations can/may be dependent on: resin handling practices, seasonal timing of each test, soil sampling practices, sampling location, tissue sampling procedures, depth of soil sample, soil properties and characteristics, crop species, plant genetics and health, plant nutrient requirements, nutrient application schedule(s) and concentration, nutrient application methods, planting density, agricultural and conservation practices and techniques, geospatial variables, and environmental/climatic variables. Corn plants are depicted within the figure, whereas the technology and correlations can be adjusted for any agricultural crop, in any planting medium, agricultural management practice and/or climate region.

Figure 14:
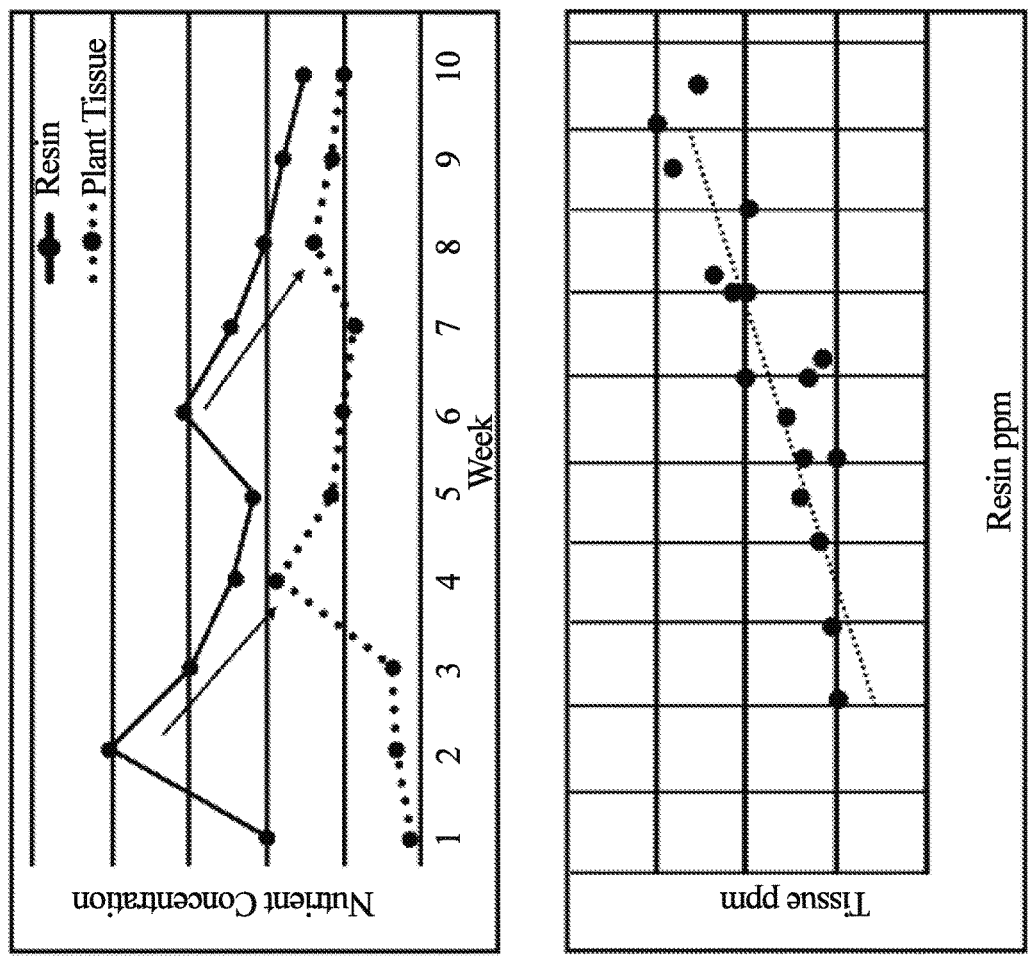

FIG. 14 shows two examples of graphs which demonstrate a correlation between soil nutrient concentration measured by resins and nutrient concentration in plant tissue. Further statistical tests solidify this correlation and establish resin systems as a leading indicator to predict nutrient absorbtion by plant tissue, validating UNIBEST methods and resin data as a prediction tool for crop needs and other agricultural modeling.

Figure 15:
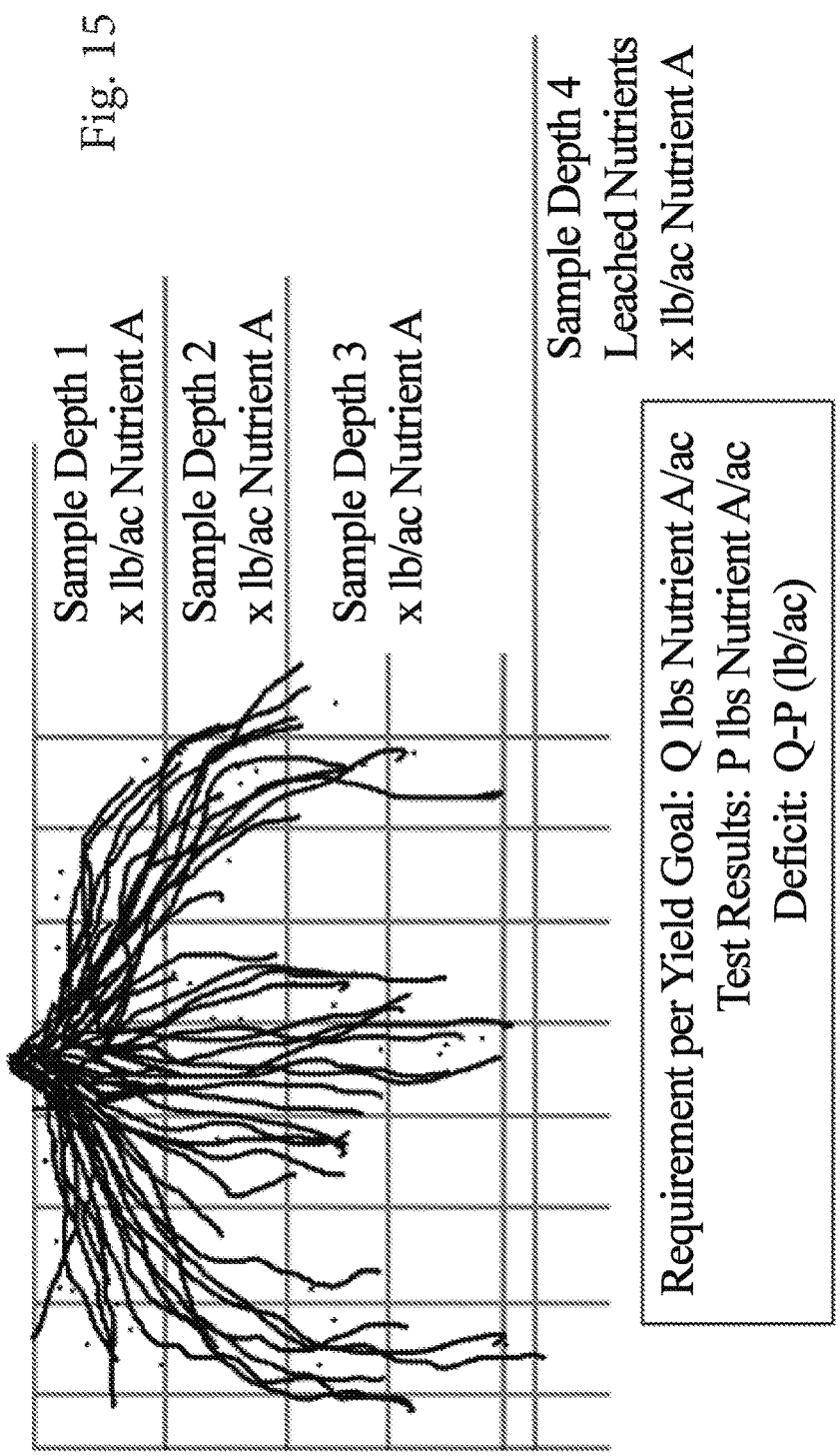

FIG. 15 is a graphic of profile nutrient availability modeling. Algorithmic conclusions based on resin profile nutrient monitoring allow for predictions of plant available nutrients within the effective rooting profile of a crop, along with predictions of nutrient losses due to leaching within soil profiles. Predictions based on resin profile nutrient monitoring algorithms can/may be dependent on: resin handling practices, soil sampling practices, soil characteristics and properties, geospatial variables, environmental and climatic variables, crop species, crop genetics and health, planting density, schedule and concentration of nutrient applications, application method for nutrients, past and present agriculture and conservation practice(s).

Algorithms:

Algorithms are used which rely on the correlation of plant tissue needs to resin measurements of soil nutrients available for plant uptake. Algorithms may be used to calculate important agricultural quantities including but not limited to crop needs/nutrient deficits, fertilizer application rates, projected soil response to fertilizer application and projected yield. These algorithms preferably combine resin data with other parameters important to soil or crop growth such as:
1. UNIBEST sampling method and analysis parameters such as: Resin soak time within the sample medium, Sampling location (in-row, between row, etc.), In-situ vs. Paste, Amount of soil added to jar, Capsule vs Cylinder, ratios of parameters (such as N to P ratio).

2. Soil parameters such as: sample depth, moisture, pH, cation exchange capacity (CEC), soil type/soil class, bulk density, organic matter, humic matter, root zone profiling/horizonation, conductivity, heavy metals, soil air, consistence, solubility, dissolved gases, percent base saturation, weight-to-volume ratio, soil color, soil compaction, soil structure, soil texture, other nutrient tests (for nutrients we don't do), herbicides, pesticides.

3. Seed/crop parameters such as: seed genetics/plant type/crop type, plant density, seed depth/timing, growth stage, projected yield, previous yield.

4. Agricultural practice parameters such as: tillage practices, cover crops, fertilizer application method (fertilizer type, liquid/solid, timing/frequency), irrigation technique, crop rotation, past land uses, seeding/harvesting timing, conservation techniques (soil drainage/tile drainage etc.), manure/compost analysis, yield goal/maintenance goal/quality goal/sustainability/environmental goal.

5. Geospatial parameters such as: climate models (temperature, rainfall, sun, seasonal models, frozen), Satellite crop modeling/remote sensing/UAV collected data, NDVI, chlorophyll index, XRF, Ultraviolet florescence, Topography, slope, aspect, land classification, variable rate models, GIS models.

6. Other parameters: a. Multivariate models (combine variables, such as tillage and moisture); b. Forestry (satellite data/remote sensors, live tree basal area, canopy cover); c. Hydroponics (nutrient solution, medium/substrate type, hydroponics technique (wick, water culture, nutrient film technique, drip, solution culture, static, continuous flow, aeroponics, passive sub-irrigation, ebb and flow/flood and drain sub-irrigation, run to waste, deep water, top-fed, deep water, fogponics, rotary).

FIG. 16 gives an example algorithm for calculating nutrient deficit, as well as a general formula that may be used for nutrient deficits or other concentration deviations. In the example nutrient deficit algorithm, the required nitrogen for the crop is determined by the yield goal and a multiplier specific to nitrogen, crop type, and the specified yield goal. The available nutrients for plant uptake is the product of resin measurements and multipliers for other important factors such as sample depth and soil type. In addition to finding deficit of nutrients, the same general formula may be used to find other concentrations of interest including but not limited to nutrients, heavy metals, pesticides, herbicides or other parameters important to soil health and plant growth. A deviation represents a deficit if positive and excess if negative. Concentration Deviation may be important for such things as fertilizer application rates, environmental/sustainable practices, efficient use of supplies/cost minimization, best management practices and to inform other procedural amendments. Optimal concentration is determined by one or multiple parameters from one or multiple databases, such as IPNI, plant genetic databases and other relevant databases. The expression for available concentration, f(Resin ppm, Parameter(s)), may be a function of the concentration measured by the resins or a function of the resin concentration and one or multiple parameters such as those listed previously in the Algorithms section.

FIG. 17 shows an example of an equation that may be used to calculate fertilizer application rate, as well as the general form of an algorithm used for Procedural Amendments. In the example, recommended fertilizer application rates are the product of nutrient deficit and multipliers for parameters that affect what proportion of the nutrients in fertilizer will become available to plants, such as soil bulk density, fertilizer type, or other parameters. The general form of the fertilizer application rate algorithm may be used for other procedural amendments that may include fertilizer application, application of other products such as water or pesticides, or other agricultural practices that may have the intention of meeting a management goal. The expression f(Concentration Deviation, Parameter(s)) may be a function of concentration deviation (such as nutrient deficit) or a function of concentration deviation and one or multiple other parameters that may include the parameters listed previously in the Algorithm section, such as UNIBEST sampling method and analysis parameters, soil parameters, seed parameters, agricultural practice parameters and geospatial parameters, and/or may include other parameters relevant to soil and agriculture.

FIG. 18 shows an example of an algorithm that may be used to predict soil response to fertilizer application, as well as the general form of an algorithm for Predicted Outcomes. The projected soil nutrient level available to plants is the sum of nutrient levels in the soil available to plants and additional nutrients that will become available to plants when fertilizer is applied. Available nutrients are calculated from resin data and other parameters. The nutrients that become available to plants from fertilizer application are equal to the product of the fertilizer application rate and a soil response multiplier which quantifies how much of the nutrients in fertilizer will become available to plants, which may depend on one or multiple key parameters such as fertilizer type, soil cation exchange capacity (CEC), moisture content and/or "Try Before You Apply" laboratory trials. The general formula of Predicted Outcomes may include quantities such as projected soil response, projected yield goals, projected maintenance goals, such as grass color for turf, projected quality goals, such as grape quality for vineyards, projected environmental/sustainability goals, or other projections of management outcomes. The predicted outcome is a function of one or multiple Procedural Amendments or a function of one or multiple Procedural Amendments and one or multiple additional parameters. Other parameters may be variables or models relevant to achieving management objectives including but not limited to the soil, seed, agricultural practices and geospatial parameters listed previously in the Algorithms section.

Figure 19:
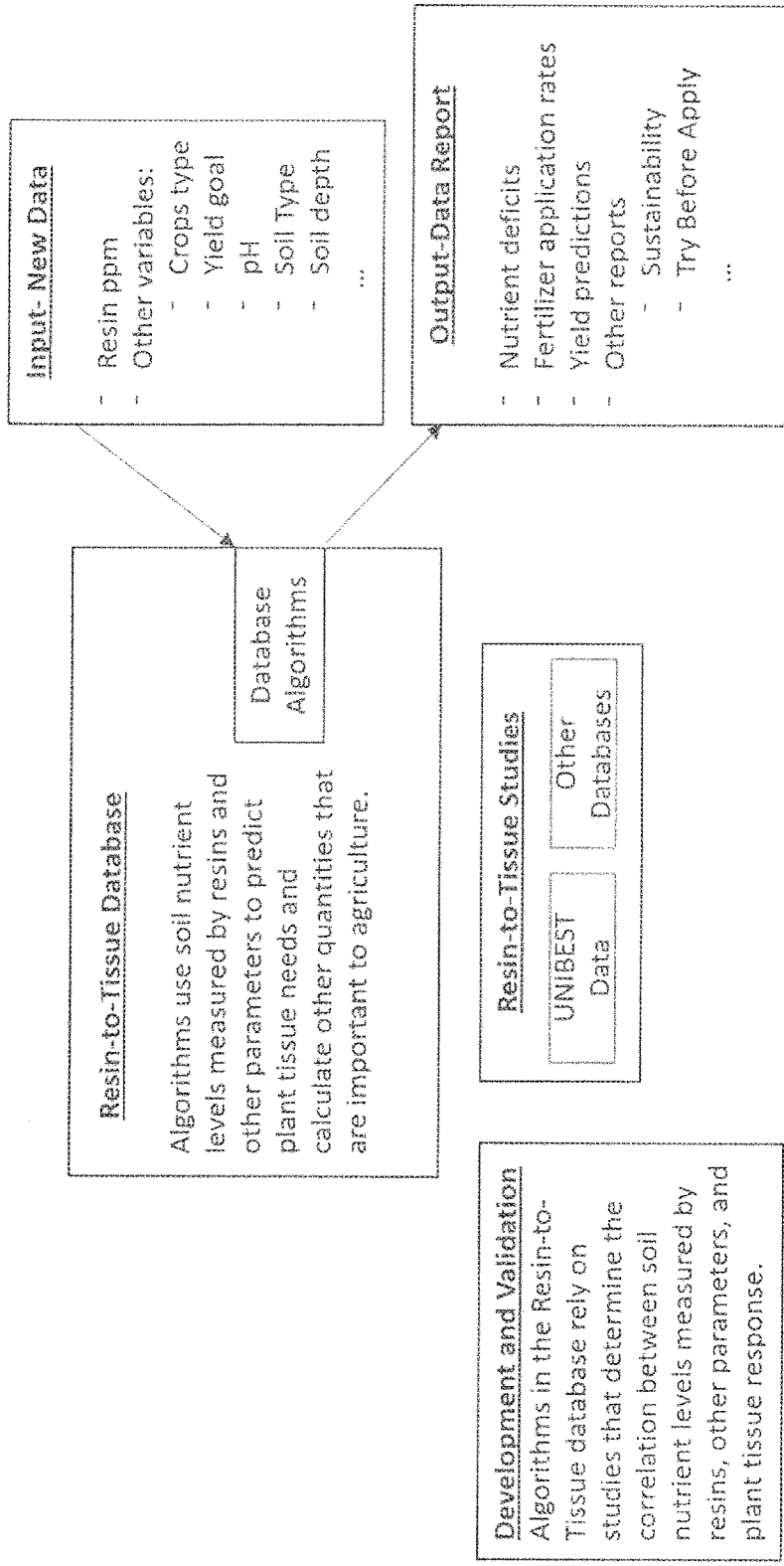

FIG. 19 shows an overview of Resin-to-Tissue based analytics. Plant tissue needs correlate with soil nutrients available for plant uptake, measured by resins or other devices. Therefore, resin data may be used as a predictive tool, along with other relevant variables to accurately report nutrient deficits, optimal fertilizer application rates, yield predictions, and other important information including but not limited to sustainability reports and "Try Before You Apply" fertilizer recommendation reports.

Example 3

An Example of Reporting and Advising

Figure 20:
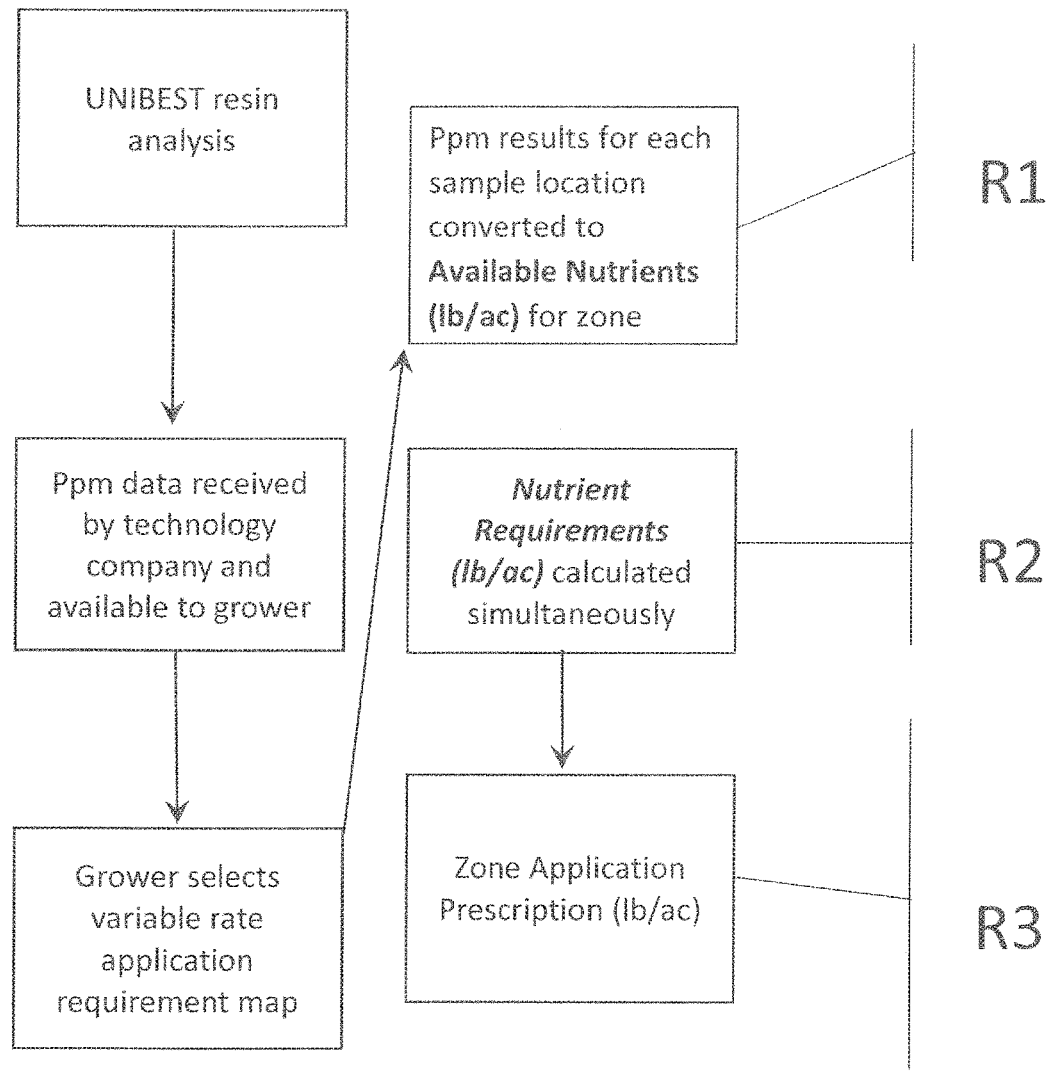
Figure 24A:
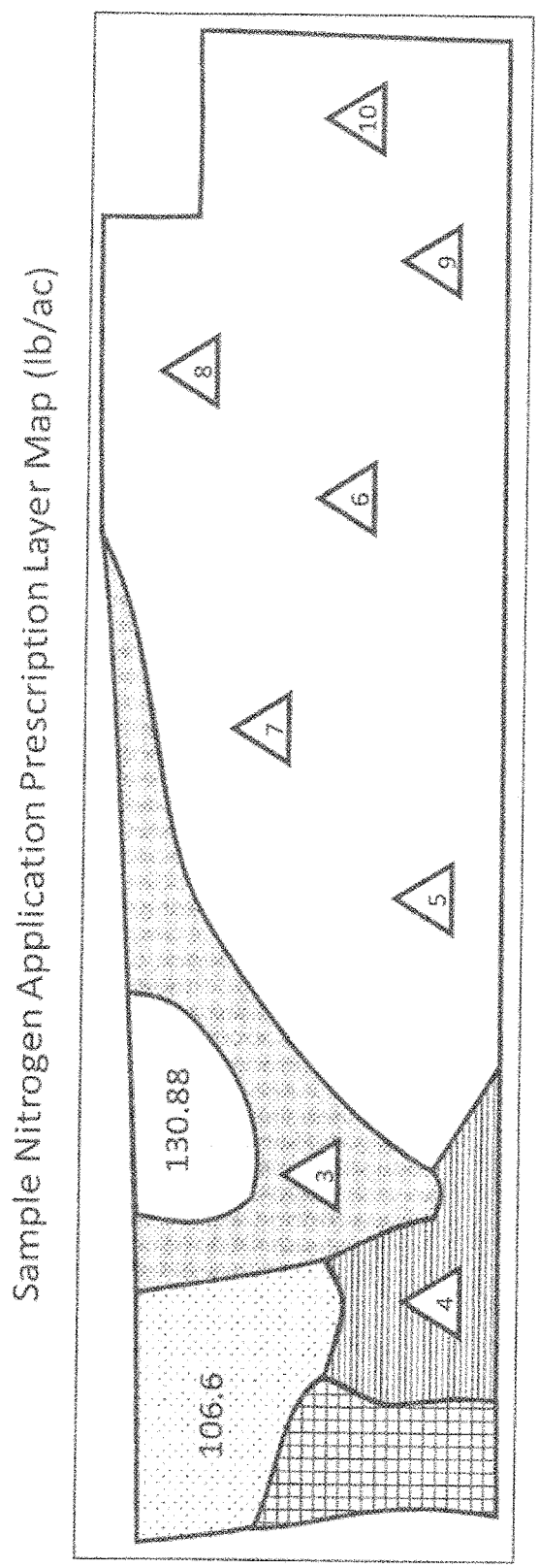
FIG. 24A illustrates a Sample Nitrogen Application Prescription Layer Map (lb/ac).
Figure 25A:
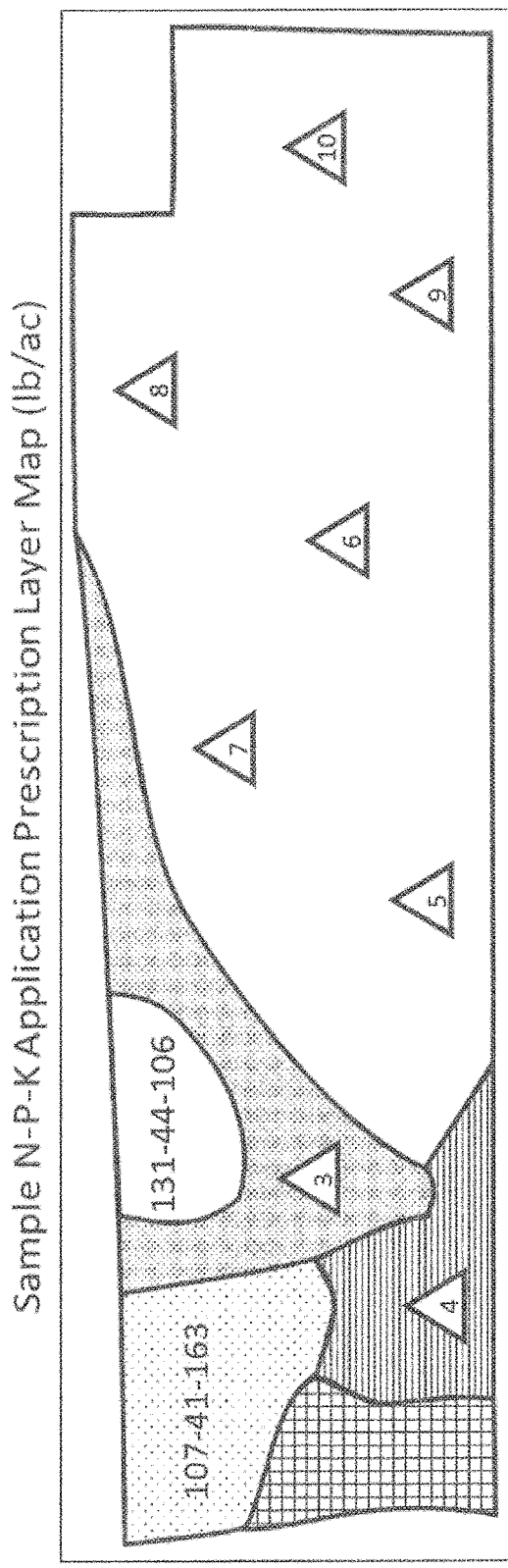
FIG. 25A illustrates a Sample N-P-K application Prescription Layer Map (lb/ac).

Regarding FIG. 20, note the following for R1, R2, and R3:
R1: Ability for specific text in cell to initiate calculation to the correct soil class multiplier line; each nutrient ppm must reference correct multiplier. Ability to take numbers listed within the depth field for each sample and perform calculations for each sample depth and calculations for zone.
R2: Ability to reference Crop listed in specific cell to correlate to the correct multipliers for calculating nutrient requirements; ability to reference each nutrient multiplier to the given yield goal for calculations; and the nutrient requirements are listed as a table and can change.

R3: The correct calculation must be performed (i.e. application prescription=required−available); need indication for negative (−) numbers as excess in profile and no application is needed; ability to take text listed in 'Zone" cell and be overlaid on a map of a field as a layer (color coded for nutrient being applied) with the correct prescriptions in the correct zones; and ability to combine nutrient application prescriptions desired and input onto map layer using specified format (e.g. N-P-K).

See the resulting data from the analysis in FIG. 21, and the resulting reports in FIGS. 22, 23A-D, 24A and B, and 25A and B, wherein in this example it is known that the crop grown is corn, the yield goal is 200 bu/ac, and the soil type is heavy.

Example 4

An Example of Apparatus and Methods of Manual Cylinder Filling

A "cylinder" herein may be a cylindrical resin sampler, for example, as in Ser. No. 14/321,380 filed Jul. 1, 2014, now U.S. Pat. No. 9,709,471, by Riess and Crass.

Some preferred features of a manual cylinder filling station may include: two plates; cylinder holding stations evenly spaced; cylinder holding stations manufactured from stainless steel, PVC, or similar non-corroding material; posts can be threaded or non-threaded; head on top of post sized greater than center post to ensure cylinder ejection; cylinder centers covered with plastic or wood button plugs to prevent resin from entering "dead space"; braces to hold plates apart during filling; can be physical brace, springs, or other device; scale or adjustable measuring device to measure out precise amount of resin; can be scaled to hold multiple cylinders; cylinder caps/lids placed manually; and/or manually transferred to hydration/packaging.

The UNIBEST Manual Cylinder Filling System is designed for a low volume environment. It uses a measuring system of either a precision scale (0.001 grams) or a device that accurately measures out the desired volume of resin/adsorbent material.

The two plates are separated and held apart via a bracing device, spring, or other device. Once separated, cylinders are placed in the holding devices and button plugs are placed over the center of the cylinder. Measured resin/adsorbent material is added to each cylinder. At completion of filling the bracing mechanism is released and the two plates are brought together and the cylinder(s) are slightly raised above the holders. The button plugs are removed and the cap is placed onto the cylinder. The cylinder is removed, cap is locked on, and cylinder is set aside.

Variations can, but not limited to, include placing measuring device on stilts above the two plates, clamps to hold the plates together, locking devices to hold the plates together, extended center posts to replace the button plugs.

Figure 26A:
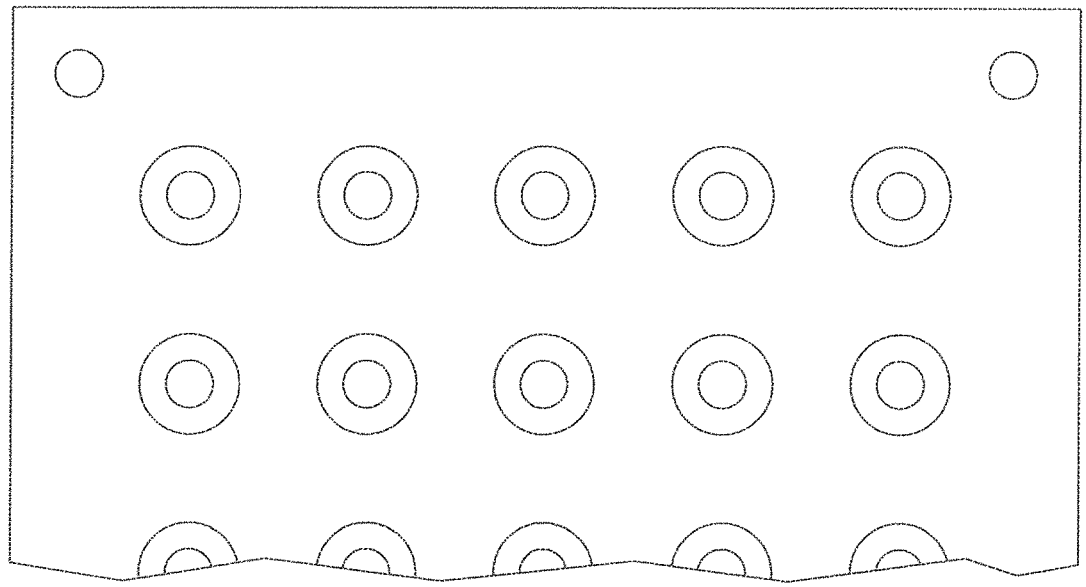
FIGS. 26A and 26B are a schematic partial top view, and a schematic side view, respectively, of a manual cylinder filling station of Example 4.
Figure 26B:
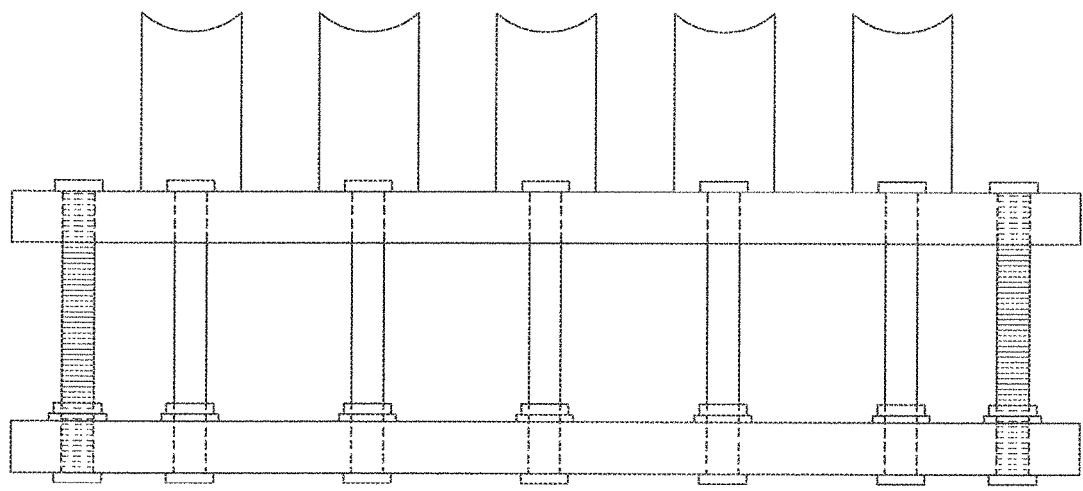
Figure 27:
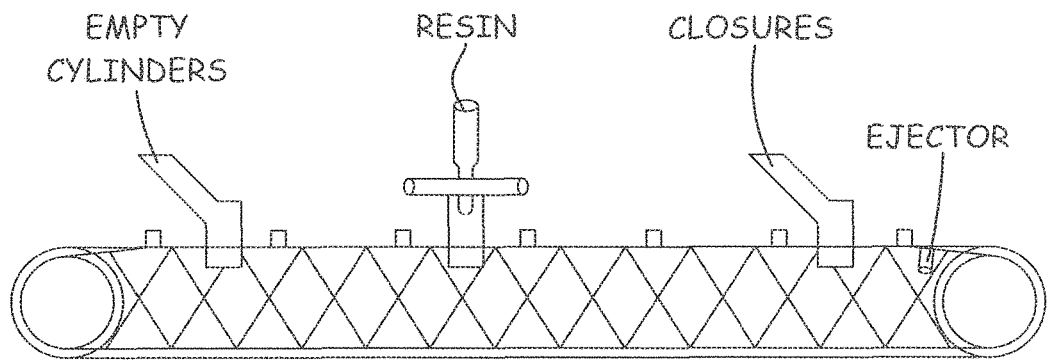
Figure 28A:
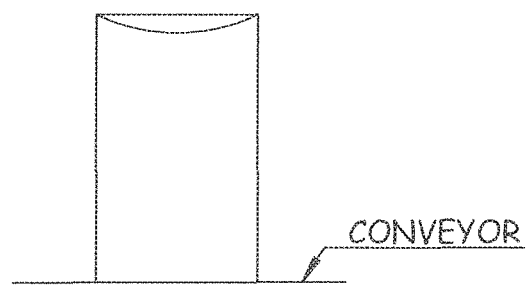
Figure 28B:
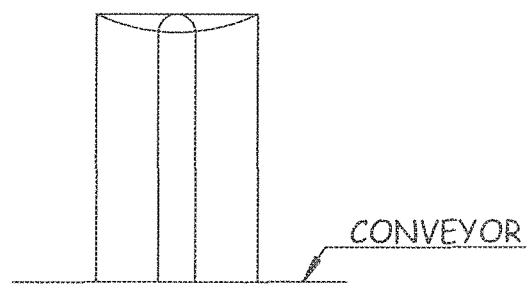
Figure 28C:
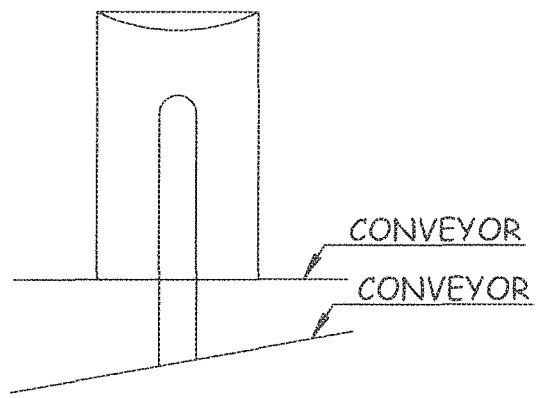
Figure 28D:
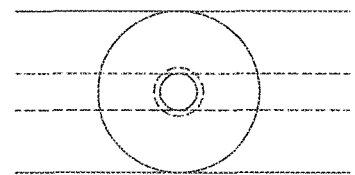

See the schematic top view in FIG. 26A and the schematic side view in FIG. 26B.

Example 5

An Example of Apparatus and Methods of Automatic Cylinder Fillings

See schematic FIGS. 27, 28A-D, 29A and B, 30, 31A and B, and 32-33, and 34A and B, and note that some preferred features of a manual cylinder filling station may include:

1. Can be electric, pneumatic, mechanical, or can be any combination thereof;
2. Two conveyor belt system; top belt contains cylinder holding device, bottom belt has center plugging rod;
3. Stainless steel posts fit to the full length of the cylinder;
4. Stainless steel, PVC (Polyvinyl chloride), or similar material for cylinder holding device;
5. Inside diameter of cylinder holding device same size as the outside diameter of cylinder;
6. Graduated and angled bin with insertion device for loading empty cylinders; can be gate, push rod, rotating spiked wheel, robotic arm, or some other device;
7. Push rod to ensure that cylinder is properly seated in holding device;
8. Pneumatic, electrical, or mechanical device to dispense/add measured amount of resin/adsorbent material;
9. Multiple dispensing devices can be added to conveyor system for adding layers of resin/adsorbent material;
10. Graduated and angled bin with insertion device to install cap; can be gate, push rod, or spiked wheel;
11. Twisting push rod to ensure cap is aligned and seated properly onto the cylinder; can be pneumatic, electrical, mechanical, or any combination thereof;
12. Ejection can be pneumatic, mechanical, robotic arm, or any other device;
13. Eject into a chute leading to a staging area;
14. Placed onto shaker table in upright position to evenly distribute resin/adsorbent material; can be accomplished via manual placement, gravity feed from ejection point, robotic arm, or any other device;
15. Place in hydration station containing inert fluid to ensure that resin/adsorbent material does not shift;
16. Can be done via manual placement, mechanical movement, robotic arm, or any other device;
17. Transfer to packaging system; can be accomplished via manual placement, mechanical movement, robotic arm; and/or.
18. Packaging can be accomplished manually, via automated system, or by other means.

Regarding FIGS. 28A-D:

The UNIBEST Automatic Cylinder Filling System is designed for high volume demand. The system uses robotics, pneumatic actuators, precision dispensers, and other mechanical/electrical/pneumatic devices. The UNIBEST Automatic Cylinder Filling System uses a conveyor belt to move cylinder holding devices from station to station. This system can be a single unit or be multi-staged, having two or more conveyors working in conjunction with each other. The UNIBEST Automatic Cylinder Filling System can be linked to an automated packaging system.

Figure 29A:
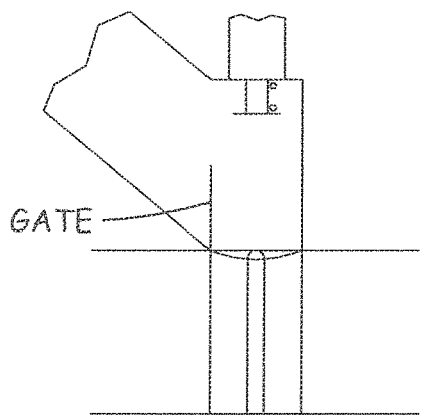
Figure 29B:
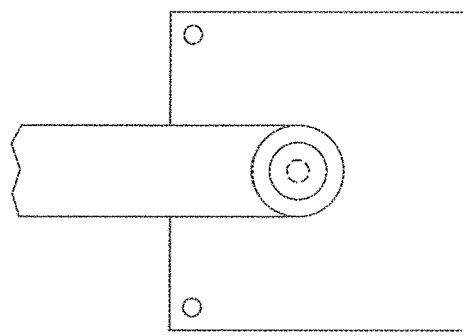

Regarding FIGS. 29A and B:

Empty cylinders are loaded into a hopper and then are loaded into a holding device using gravity, a pneumatic push rod, spiked wheel, or other device. Sensors ensure proper orientation of the empty cylinder. A stainless steel, hardened plastic, or similar material rod pushes through the hollow space of the cylinder, preventing resin/adsorbent material from entering that space.

Figure 30:
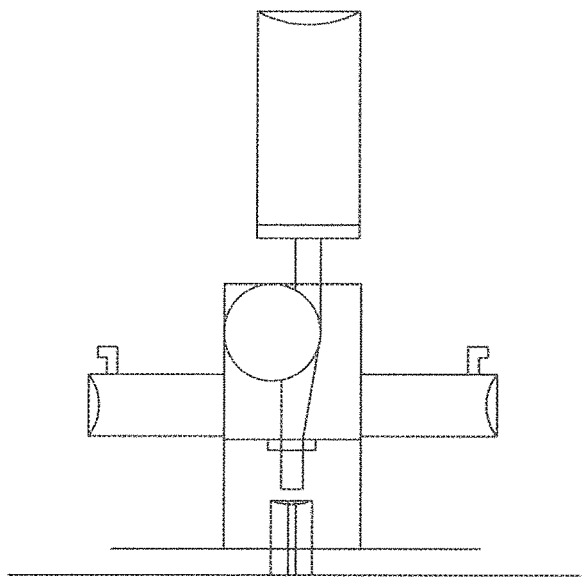
FIG. 30 schematically illustrates a filling station of the automatic cylinder filling system.
Figure 31A:
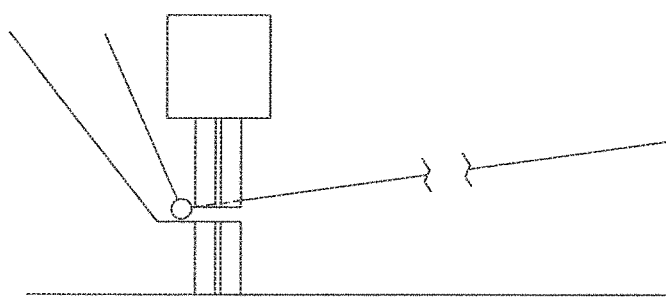
FIGS. 31A and B schematically illustrate details of a capping station of the automatic cylinder filling system.
Figure 31B:
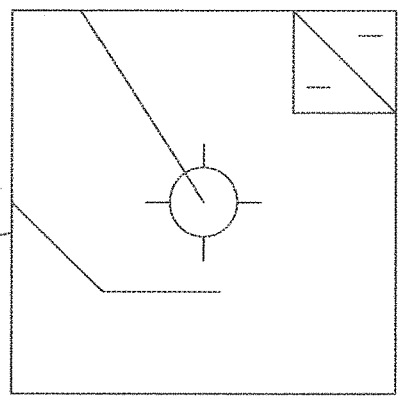

Regarding FIG. 30:

The conveyor moves the loaded cylinder holder to the filling station(s), multiple stations are employed for different resin/adsorbent layering. A measured amount of resin/adsorbent material is injected into the cylinder using gravity, a push rod, vacuum, or other method Regarding FIGS. 31A and B:

The filled cylinder is then moved to the capping station where a fitted cap is placed from a hopper using a push rod, gravity feed, spiked wheel, or other device. Sensors ensure proper orientation of the cap. A pressure sensitive rotating plunger locks the cap onto the cylinder.

Figure 32:
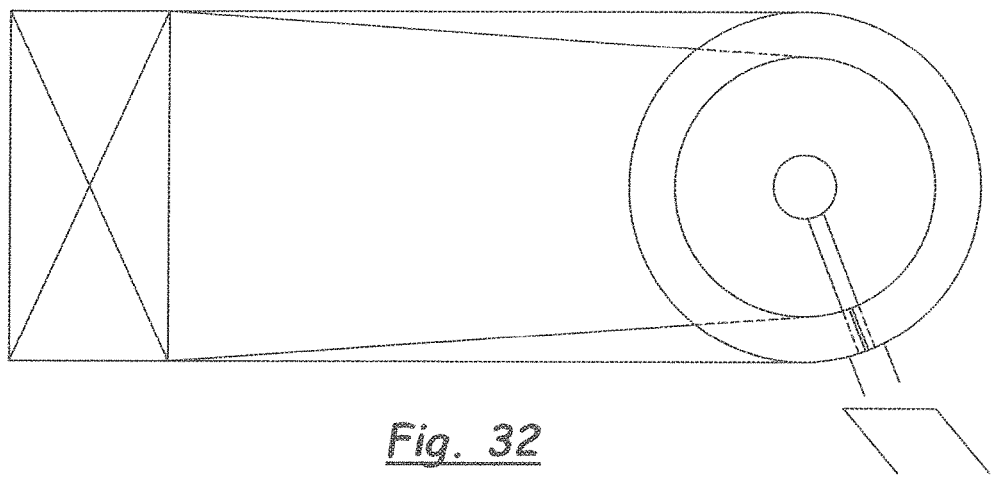
FIG. 32 schematically illustrates a cylinder ejection station of the automatic cylinder filling system.

Regarding FIG. 32:

The conveyor moves the completed cylinder to the ejection station where the cylinder is removed from the holding device using compressed air, gravity, robotic arm, or other devices. At this time the center rod is retracted.

Figure 33:
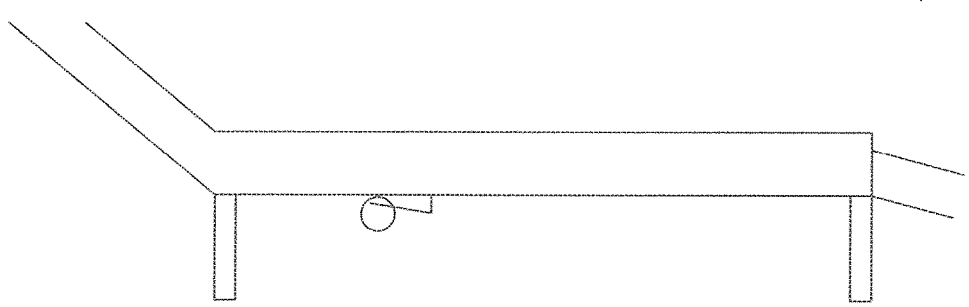
FIG. 33 schematically illustrates a cylinder manually funneled to an upright position onto a shaker table or other vibratory device.

Regarding FIG. 33:

After ejection the cylinder is funneled in in upright position manually, by robotic arm, or other method onto a shaker table, or other vibratory device, to ensure that the resin/adsorbent material is evenly distributed throughout the cylinder.

Figure 34A:
FIGS. 34A and B schematically illustrate the cylinder transferred to a hydration station.
Figure 34B:
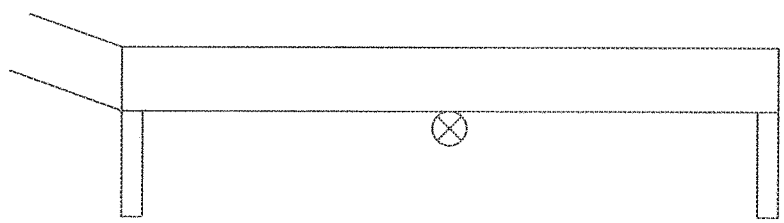

Regarding FIGS. 34A and B:

The cylinder is then transferred to a hydration station to expand the resin/adsorbent material to prevent shifting during packaging.

Example 6

An Example of Apparatus and Methods of Automatic Cleaning System

See schematic FIGS. 35-39 and note that some preferred features of an Automatic cleaning system/station may include:
1. Uses high pressure deionized (DI) water;
2. Uses PVC (Polyvinyl chloride) pipe to deliver DI water;
3. Can be used with a pressurized system or with a reservoir and pump;
4. Uses adjustable or static water jets;
5. Uses compressed air to remove excess water/cleaning agents;
6. Can be used in conjunction with UNIBEST Automatic Leaching System;
7. Trays are interchangeable with UNIBEST Automatic Leaching System;
8. Interchangeable holding trays;
9. Trays can be identified by numbering, lettering, RFID tags, barcodes, or by other visual/technological means;
10. Trays are matched to system to ensure proper alignment;
11. Trays are aligned to ensure proper placement of capsule/cylinder under corresponding emitter;
12. Side walls have small tray guides to ensure level placement;
13. Trays are notched, corner(s) modified, etched, or otherwise modified to ensure proper direction of placement;
14. Valves to cut off cleaning solution;
15. Compressed air for cleaning solution removal; and/or
16. Programmable.

The UNIBEST Automatic Capsule/Cylinder Cleaning System is designed for high volume cleaning of UNIBEST capsule(s)/cylinder(s) using pressurized cleaning agents. The UNIBEST Automatic Capsule/Cylinder Cleaning System is constructed with PVC tubing, Lexan panels, and having a large drain point to prevent water backing up and clogging. The entry points for the tubing are sealed as is the joints between the Lexan panels. The door has a rubber seal and locks during operation. The rear panel can be moved to allow for synchronizing with the UNIBEST Automatic Leaching System.

Capsules may be, for example, according to U.S. Pat. No. 5,355,736 to Skogley, and cylinders may be, for example, generally cylindrical samplers as mentioned above, for containing resin during contact with the soil, soil slurry, or soil paste, and paste, and preferably also during leaching process.

Figure 35:
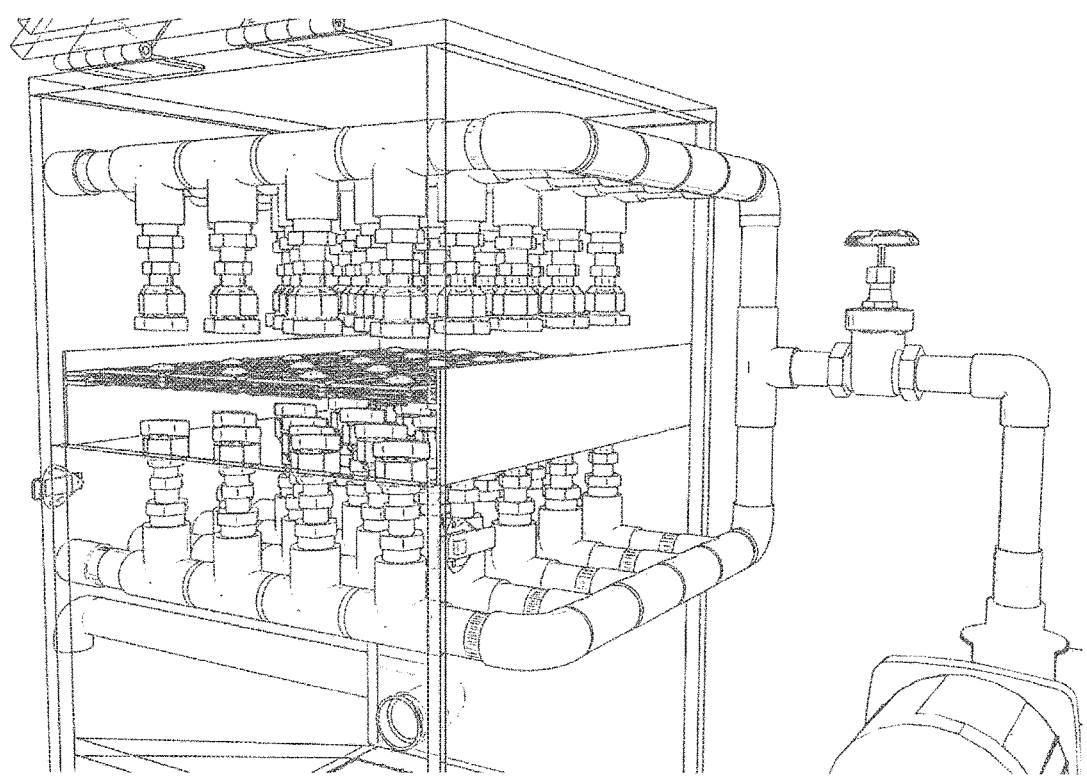

Regarding FIG. 35:

The UNIBEST Automatic Capsule/Cylinder Cleaning System is designed to work in conjunction with the UNIBEST Automatic Leaching System. The two systems can work independently or be linked together to form a continuous system. Number of samples that can be run on a single system range from 01-100.

Figure 36:
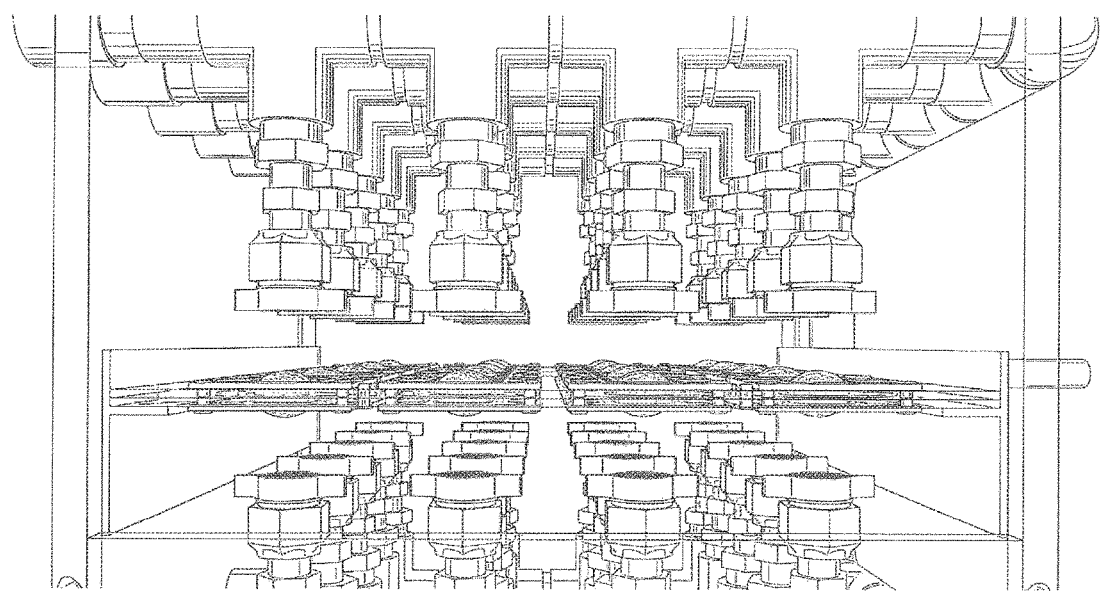

Regarding FIG. 36:

The UNIBEST Automatic Capsule/Cylinder Cleaning System can be used with deionized (DI) water to remove solids from the capsule(s)/cylinder(s), other agents may be used if needed. The DI is delivered in high pressures via a plumbed system or through a pump and reservoir system and can be heated. Directional jets, which can be static, adjustable, or a combination of both, are evenly placed above and below the capsule/cylinder holding area. Valves can be turned on or off as needed to restrict usage. The UNIBEST Automatic Capsule/Cylinder Cleaning System can be programmed with automatic valves and timers. Air jets at the nozzle point and the door are used to remove excess DI/cleaning agent.

Figure 37:
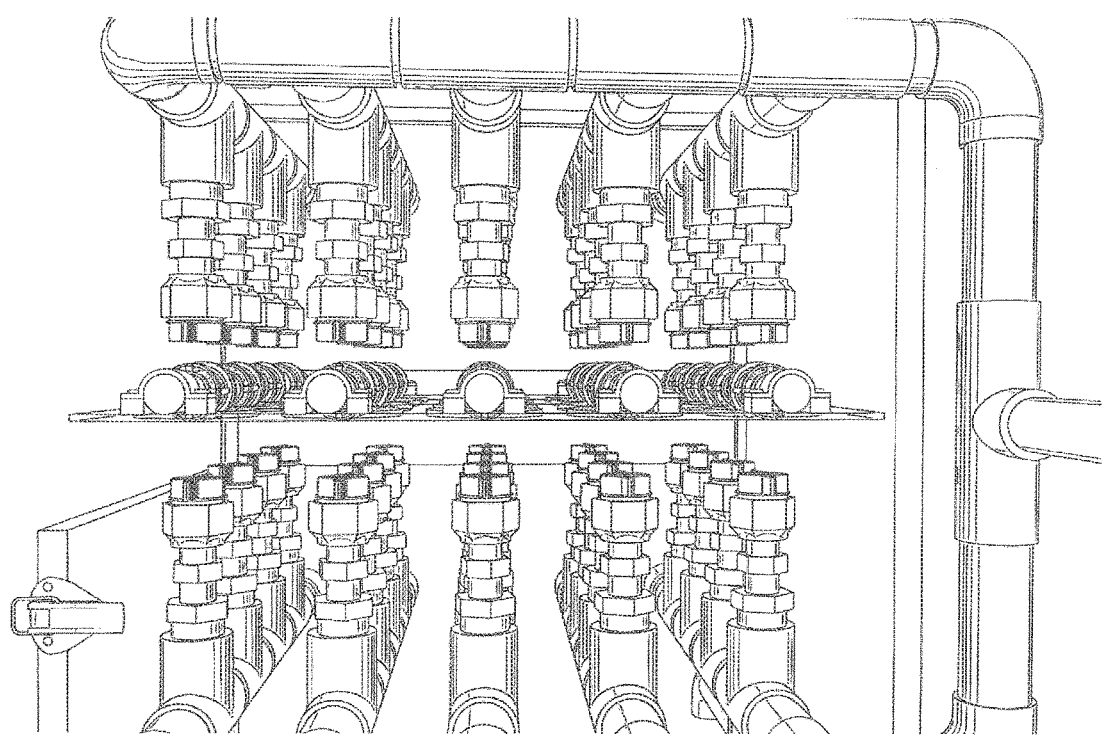

Regarding FIG. 37:

The UNIBEST Automatic Capsule/Cylinder Cleaning System can be used with deionized (DI) water to remove solids from the capsule(s)/cylinder(s), other agents may be used if needed. The DI is delivered in high pressures via a plumbed system or through a pump and reservoir system and can be heated. Directional jets, which can be static, adjustable, or a combination of both, are evenly placed above and below the capsule/cylinder holding area. Valves can be turned on or off as needed to restrict usage. The UNIBEST Automatic Capsule/Cylinder Cleaning System can be programmed with automatic valves and timers. Air jets at the nozzle point and the door are used to remove excess DI/cleaning agent.

Figure 38:
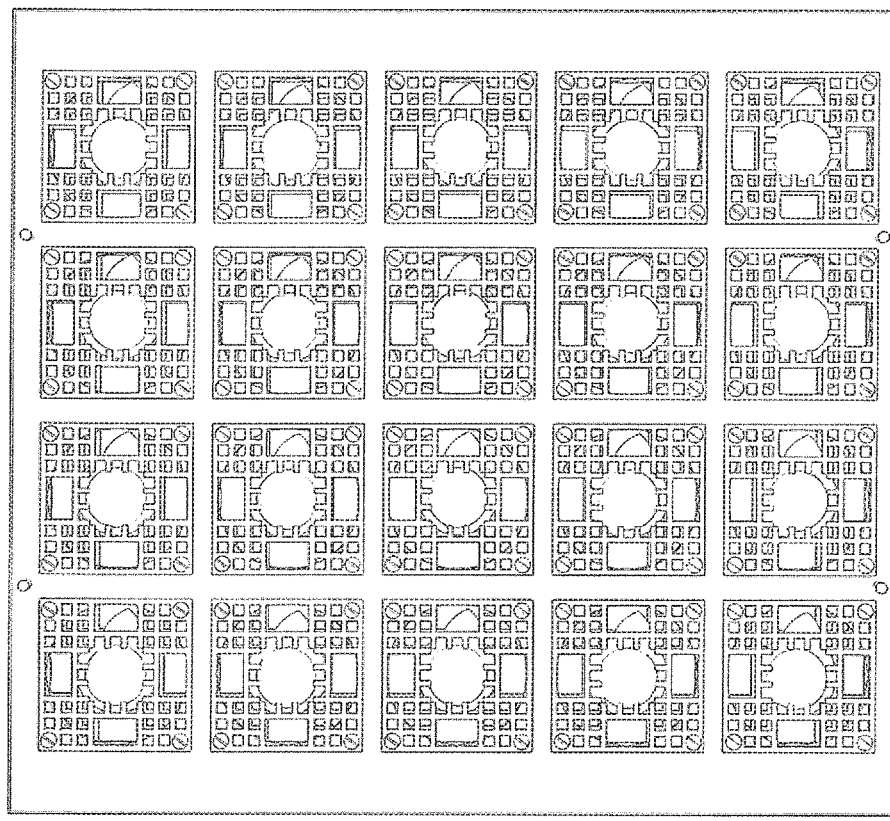

Regarding FIG. 38:

Trays are designed to hold capsules directly under the directional jets. Trays can be identified by numbering, RFID tags, barcodes, or any other method of identification. Trays are notched, corners modified, or otherwise modified to ensure proper placement into the system. Sensors can be placed to identify RFID tags, barcodes, and other types of labeling, and be linked into an automatic running system.

Figure 39:
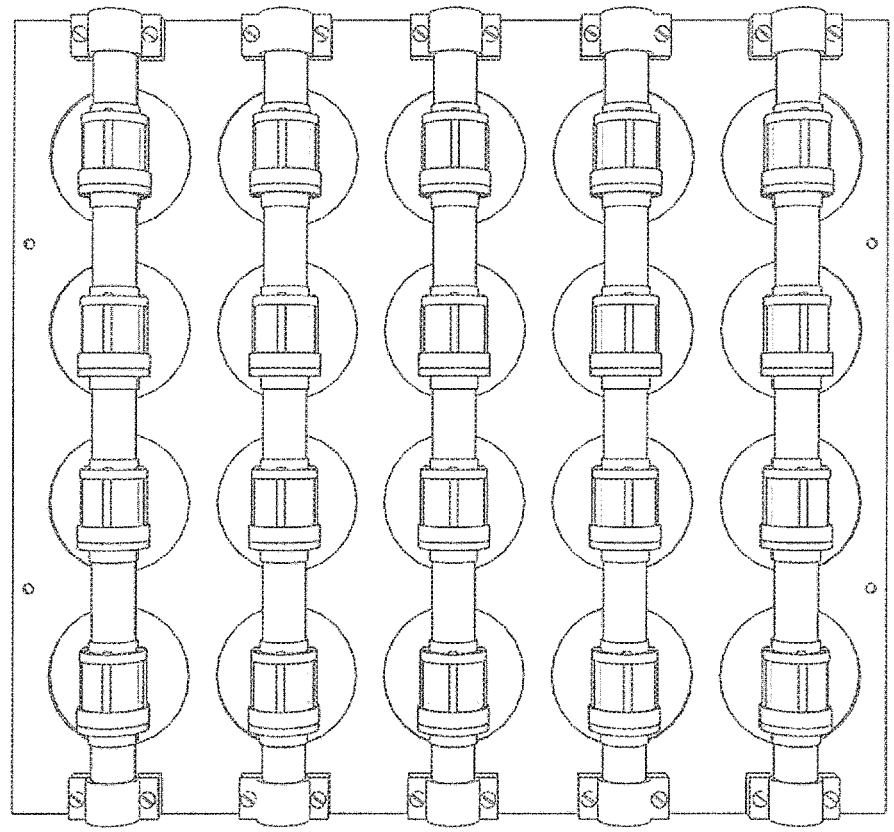
Figure 40:
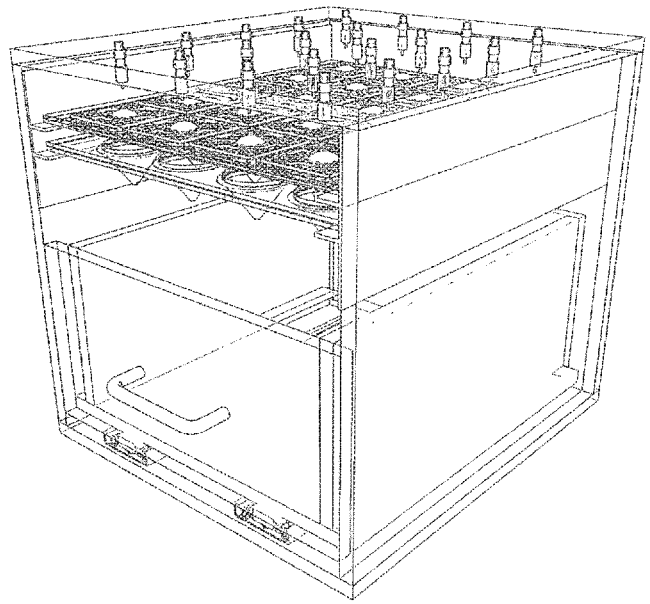
Figure 41:
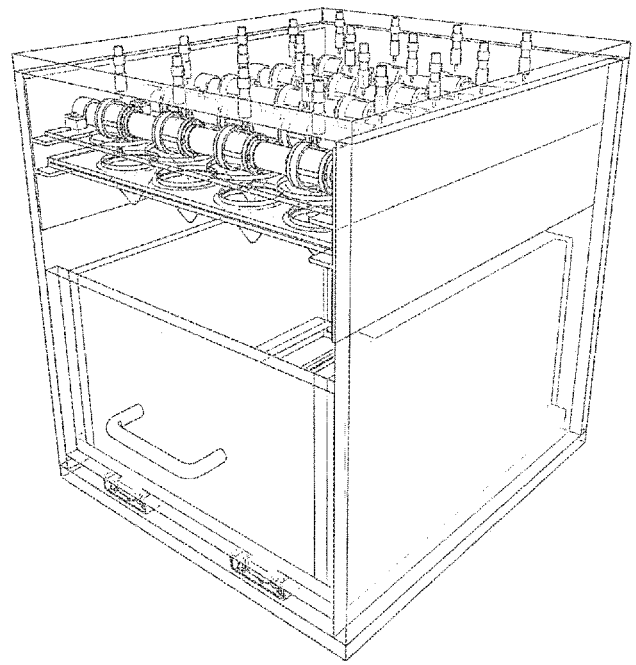

Regarding FIG. 39:

Trays are designed to hold cylinders directly under the directional jets. Trays can be identified by numbering, RFID tags, barcodes, or any other method of identification. Trays are notched, corners modified, or otherwise modified to ensure proper placement into the system. Sensors can be placed to identify RFID tags, barcodes, and other types of labeling, and be linked into an automatic running system. The placement of the cylinders can be either horizontal or vertical.

Example 7

An Example of Apparatus and Methods of Automatic Leaching System

See schematic FIGS. 40-47 and note that some preferred features of an Automatic Leaching system/station may include:
1. Uses peristaltic pump to measure out extraction fluid; can be acid, base, enzyme, solvent, or any other liquid;

2. Can be programmed for different types of leaching runs;
3. Has emitters placed to drip extraction fluid directly over capsule/cylinder to ensure proper leaching;
4. Interchangeable holding trays;
5. Trays can be identified by numbering, lettering, RFID tags, barcodes, or by other visual/technological means;
6. Trays are matched to system to ensure proper alignment;
7. Trays are aligned to ensure proper placement of capsule/cylinder under corresponding emitter;
8. Side walls have small tray guides to ensure level placement;
9. Trays are notched, corner(s) modified, etched, or otherwise modified to ensure proper direction of placement;
10. Case constructed from corrosion resistant material;
11. Number of items to be leached is adjustable;
12. Can work in conjunction with UNIBEST Automatic Cleaning System;
13. Uses small funnels to direct leachate into holding vials;
14. Capture area is customizable.

The UNIBEST Automatic Leaching System is designed for a high volume environment. Constructed from noncorrosive materials, the UNIBEST Automatic Leaching System uses acids, bases, enzymes, or other solvents to extract desired materials/chemicals from UNIBEST capsules/cylinders. The leaching agents are pumped through tubing to evenly placed emitters using a multi-channeled peristaltic pump. The pump can be programmed for different times and flow rates. Different channels on the pump can be used depending on the volume of samples being leached. Different types of leaching agents can be used in the same sample set. The UNIBEST Automatic Leaching System is designed to work in conjunction with the UNIBEST Automatic Capsule/Cylinder Cleaning System. The two systems can work independently or be linked to form one continuous system. This system can also be linked into an automated laboratory sampling system (i.e. multiple testing equipment linked via a conveyor belt). The UNIBEST Automatic Leaching System is compact and has a low power requirement. This system is easily made portable and will work for mobile laboratories. Number of samples that can be run on a single system range from 01-100.

Figure 42:
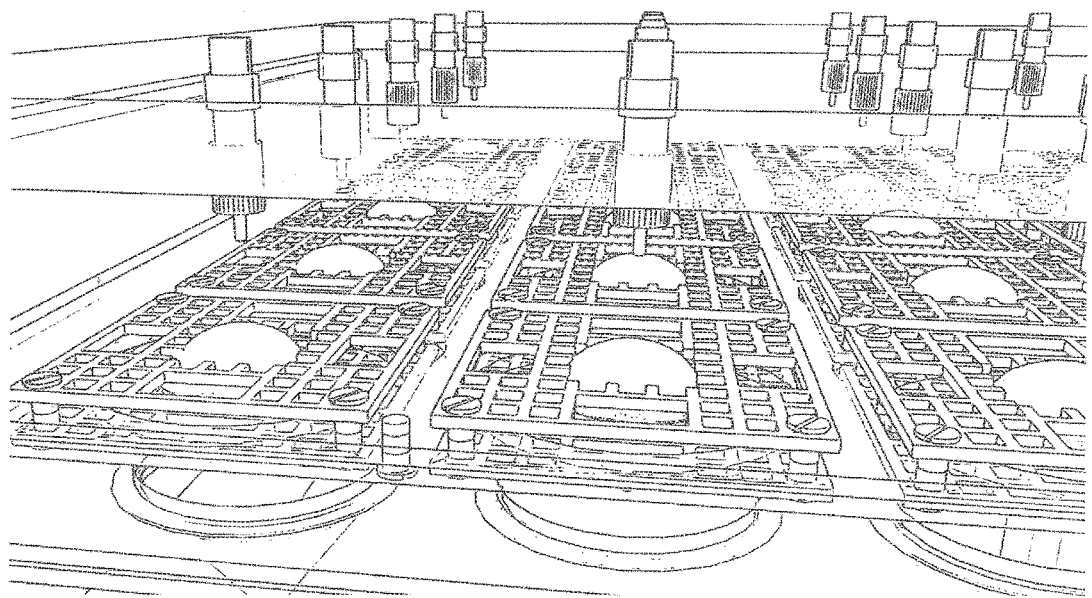

Regarding FIG. 42:

Emitters are placed so that the leaching agent is distributed directly over the center of the capsule to ensure even distribution. Emitter size varies dependent upon the nature and flow rate desired from the leaching agent. Used capsules can be removed manually, mechanically, or by robotic arm.

Figure 43:
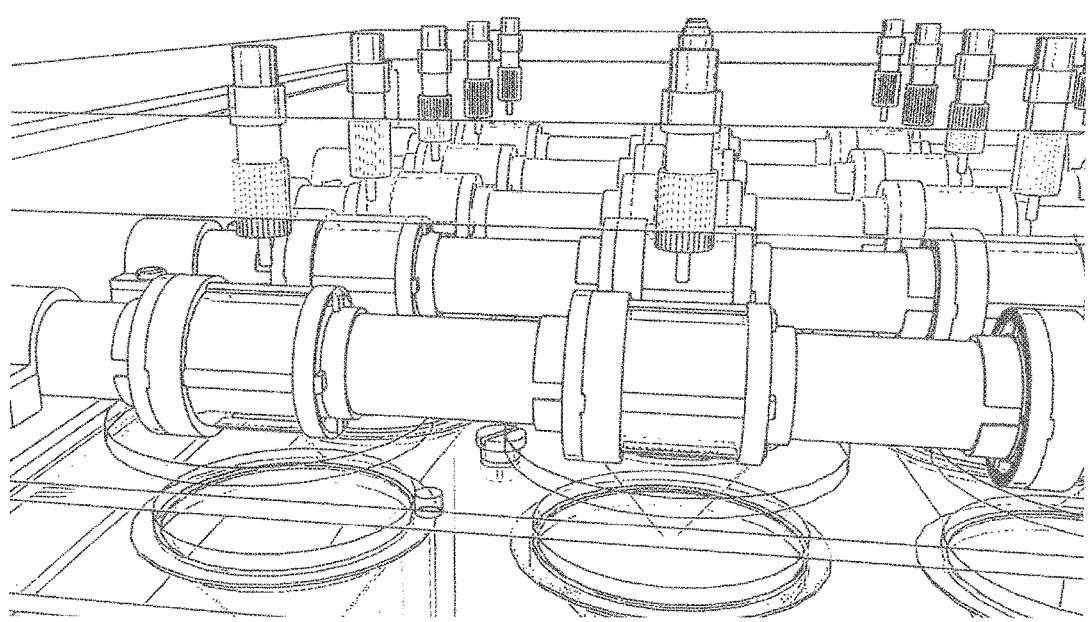
Figure 44:
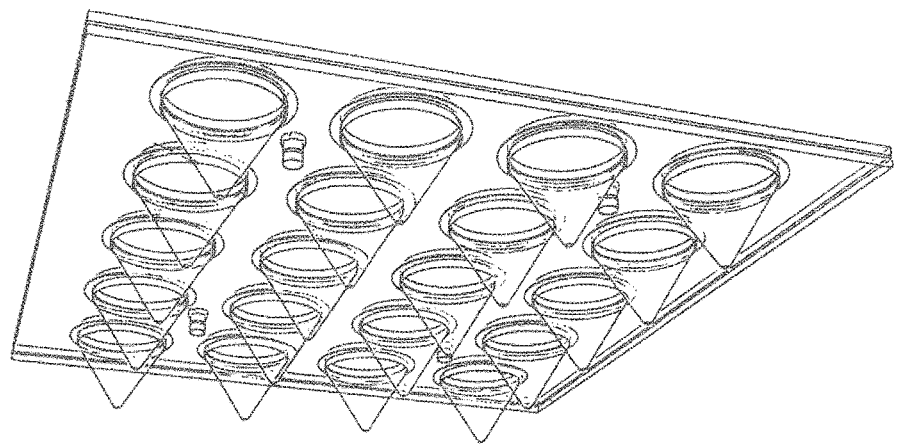
Figure 45:
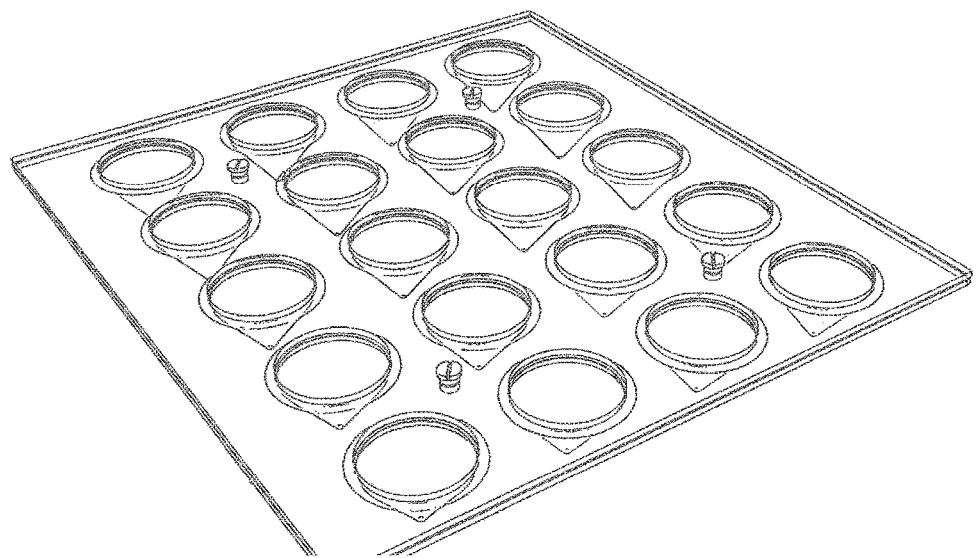

Regarding FIGS. 43-45:

Emitters are placed so that the leaching agent is distributed directly over the center of the cylinder to ensure even distribution. Emitter size varies dependent upon the nature and flow rate desired from the leaching agent. Used cylinders can be removed manually, mechanically, or by robotic arm. Funnels direct the leachate into the containers that are to be used for transferring the leachate to holding or testing areas. The funnels are designed to be used with or without filtering devices.

Figure 46:
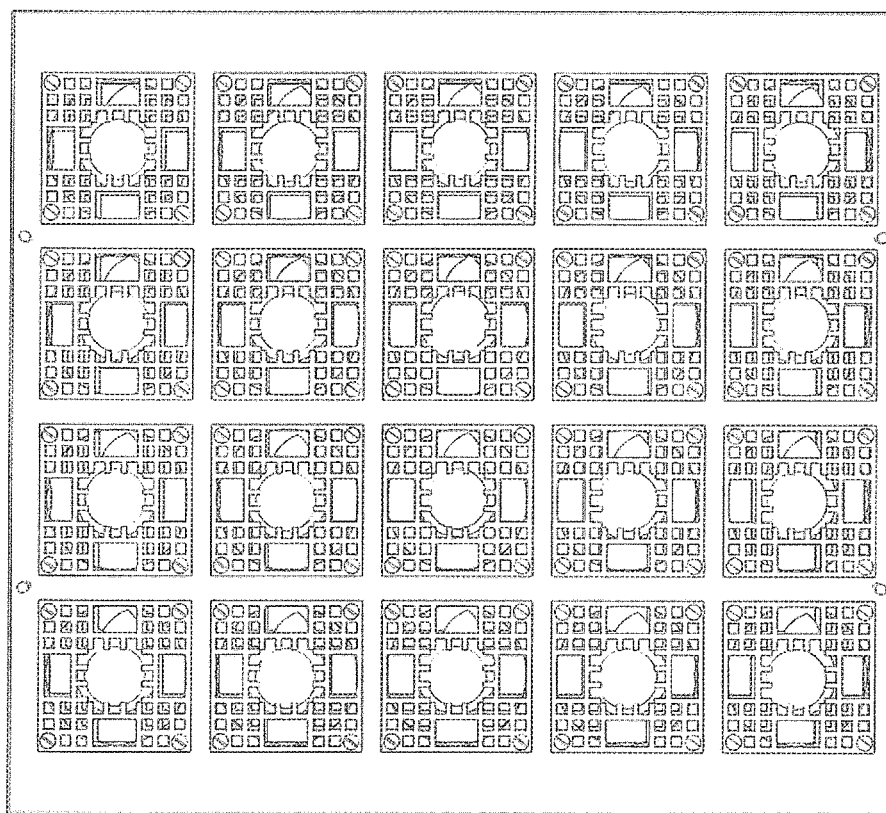

Regarding FIG. 46:

Trays are designed to hold the capsules/cylinders directly under the leaching agent emitters. The trays can be identified by numbering, RFID tags, barcodes, or any other method of identification. Trays are notched, corners modified, or other modification to ensure proper placement into the system. The UNIBEST Automatic Leaching System can be outfitted with different types of sensors for tray identification. Sensors include, but are not limited to, RFID readers, barcode readers, pressure plates, and keyed sensors.

Figure 47:
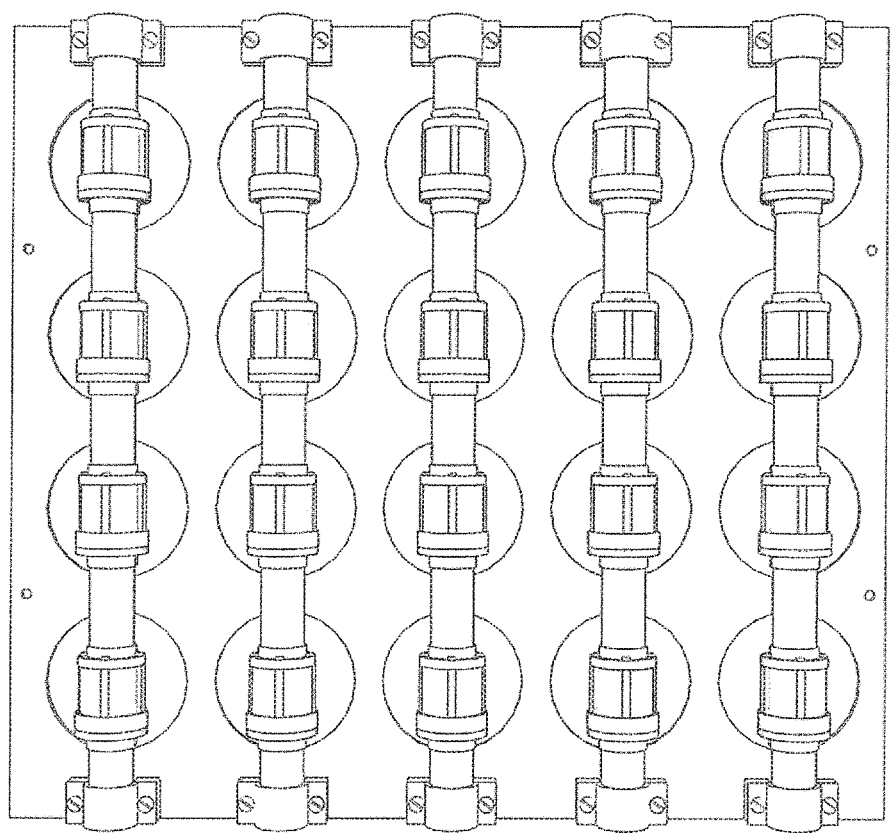

Regarding FIG. 47:

Trays are designed to hold the capsules/cylinders directly under the leaching agent emitters. The trays can be identified by numbering, RFID tags, barcodes, or any other method of identification. Trays are notched, corners modified, or other modification to ensure proper placement into the system. The UNIBEST Automatic Leaching System can be outfitted with different types of sensors for tray identification. Sensors include, but are not limited to, RFID readers, barcode readers, pressure plates, and keyed sensors. The placement of the cylinders can be either horizontal or vertical.

Example 8

An Example of Apparatus and Methods of Manual Leaching System

Figure 48:
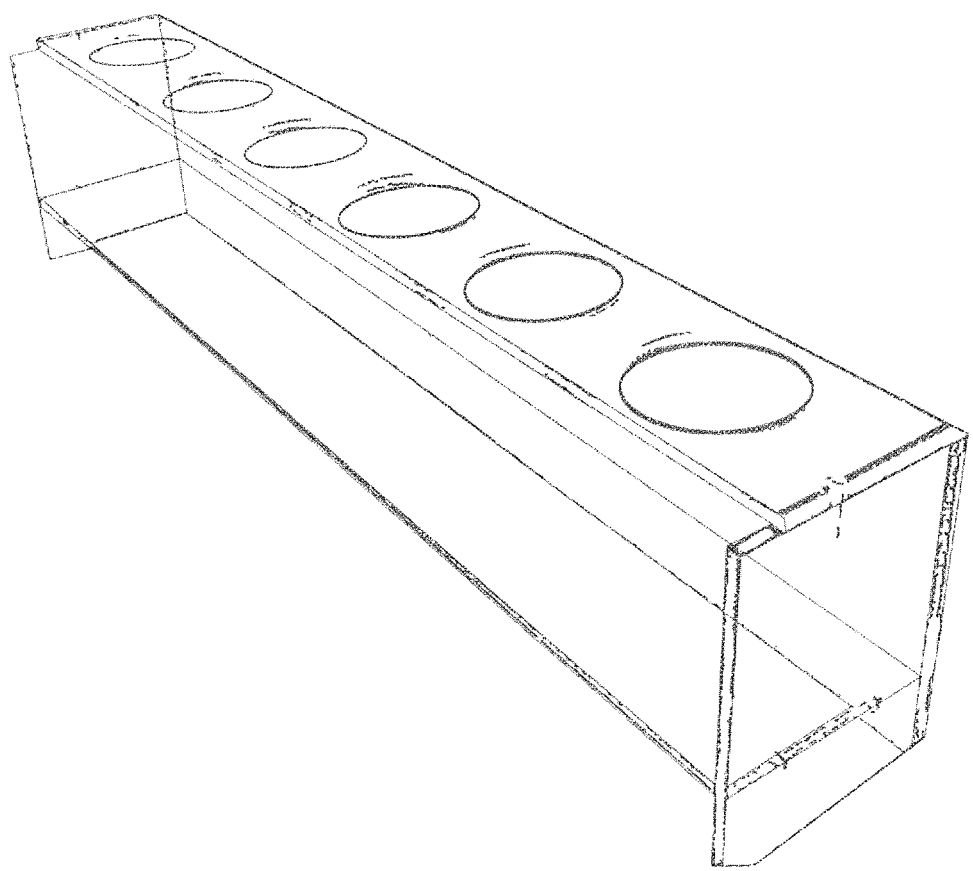
FIG. 48 schematically illustrates a manual leaching system/station of Example 8.

See schematic FIG. 48 and note that some preferred features of a Manual Leaching system/station may include:
1. Used for low volume testing;
2. Portable;
3. Easy to use; and/or
4. Constructed of chemical resistant materials.

The UNIBEST Leaching System is designed for low volume laboratory use. Constructed from noncorrosive chemical resistant materials. Each unit is designed to leach up to 6 (six) testing units, but can easily be modified for more. The system is designed to be used with reservoir systems that can be open air with a hole to facilitate desired drip rate, holding reservoir with flow control valves, pressurized bladders, injection pumps, or any other device deemed appropriate. The leachate is collected in containers located below the reservoir/drip system.

Although this disclosed technology has been described above with reference to particular means, materials and embodiments, it is to be understood that the disclosed technology is not limited to these disclosed particulars, but extends instead to all equivalents within the broad scope of this disclosure, including the text, figures, tables, and claims.

The invention claimed is:

1. A method for testing soil samples from multiple depths in an agricultural field and determining effects, on one or more available nutrient levels, of various additions to said soil samples of fertilizer or other soil treatments in a laboratory, the method comprising:

obtaining multiple field-moist soil samples in multiple regions of the agricultural field from each of multiple depths through an entire root zone for a selected plant species, the multiple depths comprising at least a first depth and a second depth;

mixing said field-moist multiple soil samples from said first depth to obtain a composite first depth field-moist sample, and mixing said field-moist multiple soil samples from said second depth, to obtain a composite second depth field-moist sample; and in a laboratory conducting steps comprising:

adding water to said composite first depth field-moist sample in a first container to form a first slurry;

and adding water to the composite second depth field-moist sample in a second contrainer to form a second slurry;

adding a portion of a blend of granular anion and cation ion-exchange resin to the first container to determine a first slurry initial available nutrient and to the second container to determine a second slurry initial available nutrient when no nutrients have been added to said first slurry and to said second slurry;

calculating a sum of the initial available nutrient of said multiple depths and comparing said sum of the initial available nutrient to nutrient requirement for desired plant growth to attain a target crop yield from the selected plant species, and calculate a nutrient deficit by subtracting said sum from said nutrient requirement;

dividing the first slurry into multiple sub-samples placed in containers, and dividing the second slurry into multiple sub-samples placed in containers;

adding different doses of fertilizer or other soil treatments to said multiple sub-samples of the first slurry, and adding said different doses of fertilizer or other soil treatments to said multiple sub-samples of the second slurry, wherein said different doses are different proportions of said nutrient deficit;

adding a portion of the blend of granular anion and cation ion-exchange resin into each of said multiple sub-samples of said first slurry and said multiple sub-samples of said second slurry;

allowing the multiple sub-samples of said first slurry and said second slurry to rest in contact with said resin for an amount of time;

separating the ion-exchange resin from said multiple sub-samples of said first slurry and said second slurry;

testing the ion-exchange resin separated from each of said multiple sub-samples of the first slurry for available nutrient level and testing the ion-exchange resin separated from each of said multiple sub-samples of the second slurry for available nutrient level, to determine the effect of said different doses of fertilizer or other soil treatments on available nutrient level in said multiple depths for recommending addition of an amount of fertilizer or other soil treatment to the field to nurture the entire root zone of the selected plant species.

2. The testing method as in claim 1, wherein said comparing comprises comparison of the initial available nutrient of each of the first slurry and the second slurry to a database or other tabulation that correlates said nutrient requirement with target crop yields.

3. The testing method as in claim 1, wherein said comparing is done for multiple specific selected nutrients.

4. The testing method of claim 1, wherein said multiple depths further comprise a third depth so that said obtaining multiple field-moist soil samples further comprises obtaining multiple field-moist samples in multiple regions of the agricultural field from said third depth in the root zone; and the method further comprises:

mixing said field-moist multiple soil samples from said third depth to obtain a composite third depth field-moist sample; and wherein said steps performed in said laboratory further comprise:

adding water to said composite third depth field-moist sample in a third container to form a third slurry; and adding a portion of the blend of granular anion and cation ion-exchange resin into the third slurry to determine a third slurry initial available nutrient when no nutrients have been added to said third slurry;

dividing the third slurry into multiple sub-samples;

adding said different doses of fertilizer or other soil treatments to said multiple sub-samples of the third slurry;

adding a portion of the blend of granular anion and cation ion-exchange resin into each of said multiple sub-samples of said third slurry; and separating the ion-exchange resin from said multiple sub-samples of said third slurry; and testing the ion-exchange resin separated from each of said multiple sub-samples of the third slurry for available nutrient level.

5. The testing method of claim 4, wherein said adding a blend of granular anion and cation ion-exchange resin comprises placing said blend into resin containers and inserting one of the resin containers into each of said multiple sub-samples of said third slurry, wherein said resin containers comprise screen having 100-500 micron screen openings so that water and small particles of soil infiltrate and contact the blend.

6. The testing method of claim 4, further comprising testing for leeching of nutrient in the field below the root zone, by obtaining multiple soil samples in multiple regions of the agricultural field from a depth below the root zone for the selected plant species;

mixing said multiple soil samples from said depth below the root zone to obtain a composite below-the-root-zone sample, and adding water to said composite below-the-root-zone sample to form a below-the-root-zone slurry;

adding a portion of the blend of granular anion and cation ion-exchange resin to determine a below-the-root-zone slurry initial available nutrient when no nutrients have been added to said below-the-root-zone slurry.

7. The testing method of claim 6, further comprising adding said below-the-root-zone slurry initial available nutrient to said sum of the initial available nutrient.

8. The testing method of claim 1, wherein said adding a blend of granular anion and cation ion-exchange resin comprises placing said blend into resin containers and inserting one of the resin containers into each of said multiple sub-samples of said first slurry and said multiple sub-samples of said second slurry, wherein said resin containers comprise screen having 100-500 micron screen openings so that water and small particles of soil infiltrate and contact the blend.

* * * * *